(12) United States Patent
Allen et al.

(10) Patent No.: US 7,364,551 B2
(45) Date of Patent: Apr. 29, 2008

(54) HAND-HELD MEDICAL APPARATUS

(75) Inventors: Jeffrey R. Allen, Poway, CA (US);
Paul E. Cranley, Lake Jackson, TX (US); Kristine L. Danowski, Midland, MI (US); James A. McIntyre, Midland, MI (US); Reed A. Schick, Midland, MI (US); Larry Sun, Sarnia (CA); Bettina M. Rosner, La Jolla, CA (US)

(73) Assignee: Kamata, LLC, Phoenix, AZ (US)

( * ) Notice: Subject to any disclaimer, the term of this patent is extended or adjusted under 35 U.S.C. 154(b) by 0 days.

(21) Appl. No.: 10/492,953

(22) PCT Filed: Nov. 8, 2002

(86) PCT No.: PCT/US02/36027
§ 371 (c)(1),
(2), (4) Date: Apr. 15, 2004

(87) PCT Pub. No.: WO03/039367
PCT Pub. Date: May 15, 2003

(65) Prior Publication Data
US 2004/0236244 A1 Nov. 25, 2004

Related U.S. Application Data
(60) Provisional application No. 60/332,349, filed on Nov. 9, 2001.

(51) Int. Cl.
*A61B 5/08* (2006.01)
(52) U.S. Cl. .............................. 600/532; 600/531

(58) Field of Classification Search ............... 600/529, 600/538, 531–533; 128/921; 73/23.3
See application file for complete search history.

(56) References Cited

U.S. PATENT DOCUMENTS

| | | | | |
|---|---|---|---|---|
| 4,935,346 A * | 6/1990 | Phillips et al. | .................. | 435/14 |
| 5,071,769 A * | 12/1991 | Kundu et al. | ................ | 436/128 |
| 5,131,387 A * | 7/1992 | French et al. | ........... | 128/205.27 |
| 5,426,032 A * | 6/1995 | Phillips et al. | .................. | 435/14 |
| 5,571,395 A * | 11/1996 | Park et al. | ................ | 204/403.1 |
| 5,656,142 A * | 8/1997 | Park et al. | ................ | 204/403.1 |
| 5,900,533 A * | 5/1999 | Chou | .......................... | 73/24.01 |
| 6,244,096 B1 * | 6/2001 | Lewis et al. | ................... | 73/23.2 |
| 6,454,723 B1 * | 9/2002 | Montagnino | ................. | 600/532 |
| 6,467,333 B2 * | 10/2002 | Lewis et al. | ................ | 73/31.05 |
| 6,540,891 B1 * | 4/2003 | Stewart et al. | .......... | 204/403.14 |
| 6,558,321 B1 * | 5/2003 | Burd et al. | ................... | 600/300 |
| 6,609,068 B2 * | 8/2003 | Cranley et al. | ................ | 702/24 |
| 6,841,391 B2 * | 1/2005 | Lewis et al. | ................ | 436/149 |
| 2003/0175992 A1 * | 9/2003 | Toranto et al. | ................ | 436/514 |
| 2003/0175993 A1 * | 9/2003 | Toranto et al. | .............. | 436/518 |
| 2003/0208133 A1 * | 11/2003 | Mault | .......................... | 600/532 |
| 2005/0084921 A1 * | 4/2005 | Cranley et al. | ................ | 435/25 |

* cited by examiner

*Primary Examiner*—Charles A. Marmor, II
*Assistant Examiner*—Navin Natnithithadha
(74) *Attorney, Agent, or Firm*—Greenberg Traurig, LLP

(57) ABSTRACT

The subject invention provides a hand-held medical apparatus (10) for detecting a predetermined component of user breath and producing a breath-component signal over a measurement time. Such breath-component signal may be correlated to a user fat metabolism indicator.

39 Claims, 5 Drawing Sheets

HAND-HELD MEDICAL APPARATUS

RELATED APPLICATIONS

This application claims the benefit under 35 U.S.C. 119(e) of U.S. Provisional Application No. 60/332,349, filed on Nov. 9, 2001.

FIELD OF THE INVENTION

This invention relates generally to a hand-held medical apparatus. More particularly, the invention relates to a hand-held medical apparatus for analyzing acetone in exhaled breath.

BACKGROUND ART

Diabetes is a chronic disease affecting many organs and body functions. The disease is caused either by a lack of the hormone insulin or by the body's inability to use insulin. Diabetes is the most common endocrine disorder. In the United States, for instance, as many as fifteen million persons have been diagnosed with diabetes mellitus, and it has been estimated that an additional ten million may have the disease without diagnosis. Although there is no cure, most cases can now be controlled adequately by a combination of medication and life style modification, including exercise, diet and weight loss.

Unfortunately, many people with diabetes have difficulty coping with the constraints that the disease puts on their lives. People find it difficult to lose weight, to maintain weight loss, to exercise regularly, to regularly take drugs, or to self-administer tests for blood glucose levels. In general, users do not receive sufficient positive support for their efforts and can become discouraged. They experience "diabetes burn-out", a feeling of hopelessness or powerlessness that contributes to abandoning efforts to manage their disease. See, for example, *Diabetes Burnout, What to Do When You Can't Take It Anymore*, W. H. Polonsky, 1999, American Diabetes Association.

People who are simply overweight or obese can experience similar barriers as those experienced by individuals managing diabetes, when attempting to control their diet and weight. Weight loss is both difficult to achieve and to sustain. Preferably, for weight loss, caloric intake should be reduced to produce an energy deficit of about 300-1000 Calories daily, which usually results in the loss of about one half to two pounds of body weight per week (NIH Guidelines, 1998).

The relatively slow rate prescribed for traditional weight loss makes the measurement of progress to goals difficult to track. Coupled with the slow rate of weight loss, factors such as daily variation in water content of the body, poor sensitivity of most scales, and slight weight gain attributable to contemporaneous improvement in muscle tone from exercise, can mask the progress being made. Many people, by contrast, expect rapid, dramatic changes in their condition. Still others expect failure and find this belief confirmed by the slow rate of change in their health. An accurate, rapid feedback mechanism is needed to help users sustain changes in their life style which will lead to sustained weight loss.

The potential for the use of exhaled breath as a diagnostic tool has long been recognized. Hippocrates taught the physician to be aware of the smell of the user's breath, as a clue to the user's condition. In 1784 Antoine Lavoisier and Pierre Laplace analyzed breath of a guinea pig, finding that an animal inhales oxygen and exhales carbon dioxide. This was the first direct evidence that the body uses a combustion process to obtain energy from food. Since that time, as many as 200 compounds have been detected in human breath, some of which have been correlated with various diseases.

It is known that a person exhales acetone in the breath when the body is in a condition of energy deficit, that is, when the body is using more energy than it is taking in through food or beverages. Ketosis is, therefore, an immediate measurable indication that a person is successfully maintaining a reducing diet. See, for example, Samar K. Kundu et al., "Breath Acetone Analyzer: Diagnostic Tool to Monitor Dietary Fat Loss", Clin. Chem., Vol. 39, No. 1, pp. 87-92 (1993).

Detection apparatus for breath components employ varying technologies. Infrared light has been used to measure breath alcohol content by Bowlds U.S. Pat. No. 5,422,485 and Paz U.S. Pat. No. 5,515,859. Sauke et al. U.S. Pat. No. 5,543,621 used a laser diode spectrometer. Other types of lasers and absorption spectroscopes have been used including cavity-ringdown spectroscopy. See, for example "Absorption Spectroscopes: From Early Beginnings to Cavity-Ringdown Spectroscopy" B. A. Paldus and R. N. Zare, American Chemical Society Symp. Ser. (1999), Number 720, pp. 49-70. Other techniques include gas-liquid chromatography ("GC"), mass spectrometry, coupled GC-Mass Spectroscopy, electrochemistry, colorimetry, chemi-luminescence, gas biosensors, and chemical methods. See, for example, "The Diagnostic Potential of Breath Analysis", Antony Manolis, Clinical Chemistry, 29/1 (1983) pp. 5-15, and "Technology Development in Breath Microanalysis for Clinical Diagnosis", Wu-Hsum Cheng, et al., J. of Laboratory and Clinical Medicine, 133 (3) 218-228 March, 1999. Among the chemical sensors are so-called electronic noses, which rely on an array of detectors to recognize patterns of physical or chemical characteristics to identify components. These sensors may rely, for example, on conductive polymers, surface acoustical wave generators, metal oxide semiconductors, fluorescence or electrochemical detection. Such sensors are commercially available from Cyrano Sciences, Pasadena, Calif., for example, and their use in detecting medical conditions such as pneumonia, halitosis and malignant melanoma has been suggested. Many of these technologies are complex, expensive and difficult to calibrate, and have not been economically adapted for individual health care use, let alone portable, hand-held analysis.

Medical apparatus for individual health care use have been disclosed. It has been suggested that self-administered breath alcohol tests could be used (See, Brown et al. U.S. Pat. No. 5,303,575) by multiple individuals at bars or other locations where alcoholic beverages are served to detect a predetermined level of breath alcohol.

WO 01/63277 and U.S. Patent Application Publication 2002-0007249-A1, herein fully incorporated by reference, disclose a personal computer breath analyzer for health-related behavior modification. In the disclosed systems, the user introduces his or her breath into an analyzer. A computer connected to the analyzer receives a breath-component signal from the sensor and converts the signal to a second signal. The disclosed systems disclose detection of acetone in breath for the detection of weight loss. However, the disclosed systems are not optimized for portable use.

U.S. Patent Application 2001-0031913-A1 discloses a home health care service for the monitoring of home health care users. This publication discloses the measurement of an analyte in urine, using a device that may be interposed in a toilet. The device detects the presence of a chemical component in the urine of the user, and generates an electrical signal that is transmitted to an Internet-based health care center. The disclosed system has not been optimized for portable use. The use of a breath-analyzing biosensor is not disclosed.

U.S. Patent Application 2001-0056328-A1 discloses a system for communications between a biosensor apparatus and a personal data assistant. The use of a breath-analyzing biosensor is not disclosed. In addition, the system requires the user to have a personal data assistant, which may be viewed by the user as having more functionality than is required, and thus, as a source of unwanted expense.

Heath care practitioners and users would find advantage in a non-invasive, hand-held, cost-effective system for the real-time monitoring of fat metabolism.

SUMMARY OF THE INVENTION

The subject invention provides a hand-held medical apparatus comprising:
a. a housing;
b. an inlet for receiving a sample of user breath;
c. a sensor for detecting a pre-determined breath component of said user breath and producing a breath-component signal over a measurement time;
d. a sensing electrical circuit in electrical communication with said sensor for sensing said breath-component signal, wherein the magnitude of said breath-component signal is a function of the concentration of said pre-determined breath component in said breath sample to be received into said inlet;
e. an analog to digital converter in electrical communication with said sensing electrical circuit for converting said breath-component signal to a digital signal;
f. a microprocessor for processing said digital signal into at least one of a data signal and a user fat metabolism indicator; and
g. a display in electrical communication with said microprocessor for displaying said user fat metabolism indicator.

The inventive apparatus is expected to assist a user in modifying health related behaviors, particularly weight loss. In particular, the inventive apparatus is expected to provide a measurement that is more reflective of the user's recent choices than other typical measurement devices, such as scales, tape measures, and fit of clothing. The inventive apparatus is expected to enable the user to readily recognize progress made and the lack thereof, and associate the same with the dietary and exercise choices that he or she has recently made. The portable and hand-held nature of the inventive apparatus is expected to be advantageous, in that it will accord the user with convenience and privacy during use.

These and other embodiments are more fully described in the Detailed Description, in conjunction with the following figures.

DETAILED DESCRIPTION OF THE PREFERRED EMBODIMENT

Figure 1:
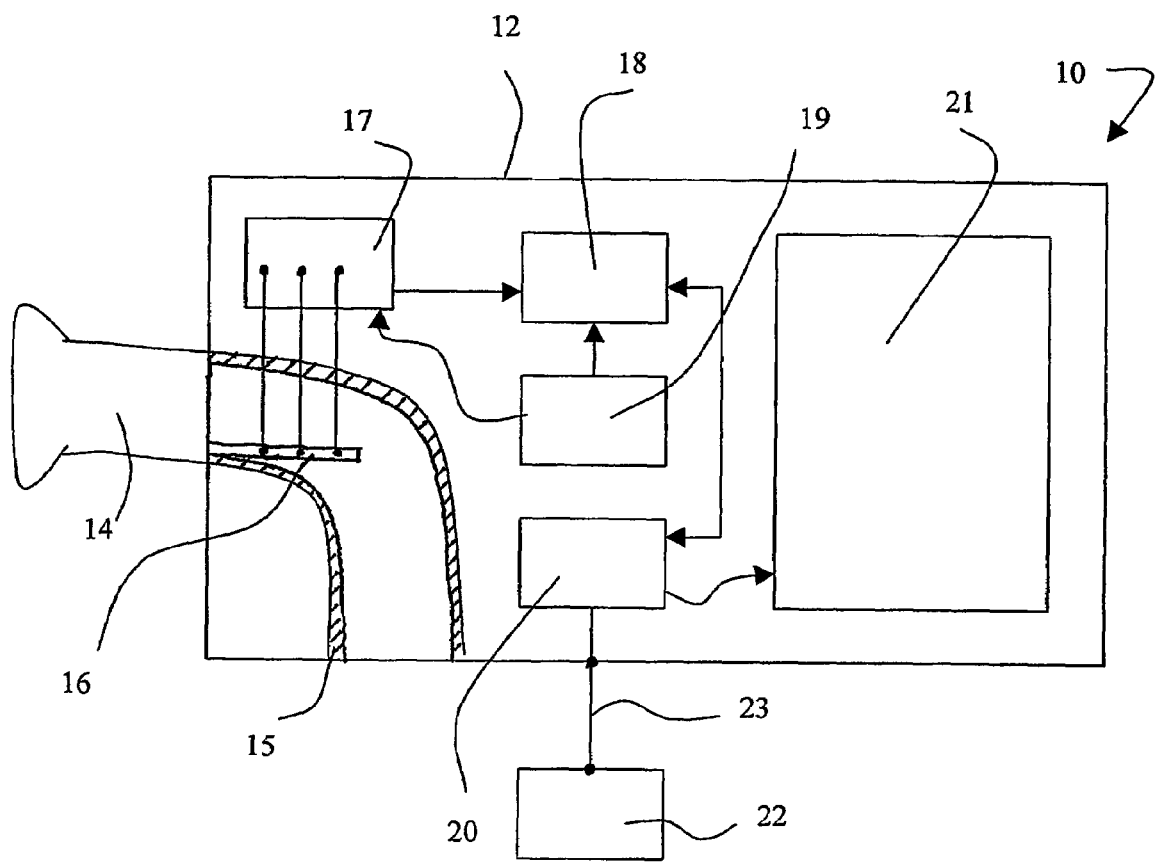
FIG. 1 is a schematic diagram of a hand-held medical apparatus of the present invention incorporating an electrochemical biosensor for the detection of acetone in breath.

Unless otherwise expressly noted in this specification, the singular forms "a", "an" and "the" include plural referents unless the content clearly dictates otherwise. Thus, for example, reference to "a pre-determined breath component" includes mixtures of pre-determined breath components. Unless otherwise expressly noted in this specification, all technical and scientific terms used herein have the meaning as commonly understood by one of ordinary skill in the art to which the invention pertains. Unless otherwise expressly defined in this specification, the following terms will be used in accordance with the accompanying definitions.

"Hand-held" means of a size sufficiently small to permit an adult human user of the medical apparatus to generally support the medical apparatus on the palm and optionally the adjacent fingers of one of his or her hands. Typical dimensions are less than about three inches (7.62 cm) by five inches (12.70 cm) by one inch (2.54 cm). Examples of other hand-held objects include Palm Pilot™ personal data assistants and pocket calculators.

"Inlet" means an opening to the medical apparatus which is in communication with the sensor, through which a sample of user breath is introduced into the medical apparatus for detection or measurement of a pre-determined breath component by the sensor.

"User breath" means a sample of breath exhaled from the user into a breath inlet of the medical apparatus, which user breath may contain a pre-determined breath component.

"Sensor" means a device comprising means for recognizing the pre-determined breath component and means for transducing a signal based upon such recognition.

"Pre-determined breath component" means a potential component of user breath to be detected by the sensor, which potential component is a by-product of fat metabolism Detection or measurement of at least one such pre-determined breath component will permit the determination of whether or not the user is metabolizing fat at the time that a given sample of user breath is detected by the sensor. One exemplary pre-determined breath component is acetone.

"Breath component signal" means an electrical or optical signal generated by the sensor when the sensor is exposed the pre-determined breath component.

"Measurement time" means the period of time over which the sensor produces the breath component signal.

"Sensing electrical circuit" means an electrical circuit adapted for communicating the breath component signal from the sensor to the analog to digital converter. The sensing electrical circuit optionally and preferably includes an amplifier for amplifying the breath component signal prior to communication to the analog to digital converter.

"Operative connection" means a connection between two units, objects or devices which is suitable to permit physical communication or electrical communication from one to the other or to permit the two units, objects or devices to work in concert with one another to achieve a pre-determined cooperative effect.

"Analog to digital converter" means a device for converting an analog breath component signal received from the sensing electrical circuit to a digital signal receivable by the microprocessor.

"Microprocessor" means a computer processor contained on an integrated circuit chip, preferably including memory and associated circuits.

"Data signal" means a signal derived from the digital signal, which is meaningful to the user. By way of non-limiting example, data signals include a binary signals (indicating the presence or absence of detectable levels of the pre-determined breath component in the user breath), as well as quantitative signals (indicating the concentration of the pre-determined breath component in said user breath).

"User fat metabolism indicator" means a numeric, audio, visual, audiovisual and/or tactile signal for display to the user. By way of example, the user fat metabolism indicator may be the data signal itself. In the alternative, the user fat metabolism indicator may be an expression of the data signal, for instance, a display of "detected" or "non-detected" or a symbol therefor, such as a green light (detected) or a red light (not-detected), or a bell (detected) or buzzer (not-detected). Alternatively, the user fat metabolism indicator may signal whether or not the concentration of the predetermined breath component falls within a pre-designated range (in which case, the user fat metabolism indicator may be, for instance, "recommended level for safe weight loss", "lower level than recommended level for effective weight loss", or "higher level than recommended for safe weight loss"). Likewise, the user fat metabolism indicator may indicate progress in a weight control program.

"Electrochemical biosensor" means a sensor which detects electricity generated from a biochemical transformation of the pre-determined breath component (or a reaction product or by-product thereof). In a preferred embodiment, said electrochemical biosensor will comprise a disposable electrode system, which in turn comprises a working electrode, reference electrode, and a counter electrode; a physical support; and an enzyme that selectively targets the pre-determined breath component. In one embodiment, the electrodes will be screen-printed onto the physical support. In one embodiment, the enzyme will be immobilized in a gel or polymeric medium, which is retained in communication with the electrodes on the surface of the electrochemical biosensor.

"Personal data assistant" means a hand-held computing device having suitable power sources and electronics, for example, memory means, software means and display means, which is suitable to receive a data signal from a microprocessor within the hand-held medical apparatus, store the data signal as stored data, convert the data signal to a user fat metabolism indicator, and display the user fat metabolism indicator (or related information) for observation by the user. The personal data assistant may be a commercially available personal data assistant, such as a Palm™ personal data assistant, having a port suitable for providing a removable operative connection between the personal data assistant and hand-held medical apparatus. In the alternative, the personal data assistant may be a specially adapted device having a housing, wherein the sensor, suitable power sources and electronics, for example, memory means, software means and display means, are retained within or are fixedly attached to and/or retained within the housing.

We will now describe our invention in connection with the accompanying figures, wherein like numerals are used to designate like parts in each drawing. FIG. 1 provides a block diagram of one embodiment of the claimed hand-held medical apparatus. Hand-held medical apparatus 10 comprises housing 12. Apparatus 10 has an inlet 14 in communication with conduit 15. In one preferred embodiment, inlet 14 is disposable and/or detachable from housing 12.

An electrochemical biosensor 16, preferably comprising a working electrode, counter electrode and reference electrode, is in electrical communication with sensing electrical circuit 17. Sensing electrical circuit 17 is in electrical communication with an analog to digital converter 18. A constant voltage circuit 19 is in electrical communication with the sensing electrical circuit 17 and the analog to digital converter 18. A battery, not shown, is used to power the hand-held medical apparatus 10 and, of course, other power sources can be used such as a converter. The digital signal from the analog to digital converter 18 is communicated to a microprocessor 20. The microprocessor 20 is in electrical communication with a liquid crystal display 21 and a personal data assistant 22.

A preferred enzyme system used in the electrochemical biosensor 16 is described in greater detail below. A more general description of the enzyme system is disclosed in U.S. Provisional Patent Application Ser. No. 60/332,349 filed Nov. 9, 2001, herein fully incorporated by reference. Details of suitable electrode designs and electronic components that can be used herein are described in U.S. Pat. Nos. 5,571,395 and 5,656,142, herein fully incorporated by reference.

Hand-held medical apparatus 10 can include a sampling device, not shown. The sampling device captures a portion of the user's exhaled breath, preferably alveolar breath from deep within the lungs. The breath sample may be captured in a chamber or in a trap or both. Generally, traps fall into three categories: chemical; cryogenic, cold trapping or condensing; and adsorptive. Highly preferred is a trap that utilizes a compressible, porous material, such as open cell polyurethane foam, which can hold water or buffer solution. The porous material allows the water or buffer solution to be held in a dispersed state with a high surface area. As the user blows through the porous material, acetone is partitioned into the water or buffer solution according to Henry's Law. The porous material can then be compressed to release the water or buffer solution that now contains the acetone onto the electrochemical biosensor 16. Alternatively, the water or buffer solution can be conducted out of the porous material by a capillary channel at the tip of the electrochemical biosensor 16. A mass air sensor system, not shown, can be positioned in the conduit 15 to better assure that a sufficient volume of user breath has been introduced into the inlet 14 of the hand-held medical apparatus 10.

Hand-held medical apparatus 10 can also include data storage means, not shown, in electrical communication with the microprocessor 20. Microprocessor 20, for example, can convert a data signal to a user fat metabolism indicator. Liquid crystal display 21 displays to the user one or more elements of data, including but not limited to the data signal and the user fat metabolism indicator.

Hand-held medical apparatus 10 can further comprise user input means, not shown, such as a keyboard, mouse, voice recognition device, or an electronic stylus, through which the user can introduce additional information to microprocessor 20. Apparatus 10 preferably further comprises communication means 23, by which information, including but not limited to the data signal or user fat metabolism indicator, is transmittable to, for example, the personal data assistant 22 and/or to a computer (not shown) for data storage and/or further processing. Communication means 23 include but are not limited to means for establishing a wired connection, wireless connection, telephonic connection or Internet connection between microprocessor 20 and an external computer. Preferably, such external communication means (as well as the personal data assistant means themselves) will include data encryption means for preserving the privacy of individual user data. A clock, not shown, will preferably be provided and connected to or incorporated in microprocessor 20 or the personal data assistant 22. Personal data assistant 22 can alternatively be located within housing 12.

In one preferred embodiment, hand-held medical apparatus 10 will comprise one or more additional sensors, not shown. These sensors may include an environmental thermometer, a barometer, a hygrometer, or other sensors for determining the condition in which the sample is given. The sensors may also include additional user sensors, such as a user thermometer, heart rate or blood pressure sensors. Another sensor might be a camera or voice recognition device to confirm the user's identity as well as to record more information on the user's health. The output from such sensors can be communicated to microprocessor 20 and/or the personal data assistant 22 and optionally stored in data memory. The personal data assistant 22 can optionally be in one or two way communication directly or indirectly with a computer, such as by way of the Internet.

Hand-held medical apparatus shown in FIG. 1 can be used by first wetting the electrochemical biosensor 16 and inserting it through the side of the housing 12 into the conduit 15, breathing into the inlet 14 for a length of time sufficient to equilibrate the electrode biosensor 16 with acetone from the user breath and then pressing an initiating button. The sensing electrical circuit applies a voltage to the electrochemical biosensor 16 (for example, about 350 millivolts between the working and reference electrodes; determining the electrical current between the working electrode and the counter electrode) and reads the electrical current between the working electrode and the counter electrode after a predetermined time, for example, after thirty seconds (or more preferably such current is measured over time as described below, to obtain an integrated signal) as the breath-component signal. The analog to digital converter 18 converts the breath-component signal to a digital signal sent to the microprocessor 20. The microprocessor 20 sends a data signal or user fat metabolism indicator to the liquid crystal display 21 and to the personal data assistant 22. Prior to use, the electrochemical biosensor 16, will preferably be calibrated by exposing it to known concentrations of solutions of the pre-determined breath component (for instance, acetone) in water, and deriving a standard curve.

The hand-held medical apparatus will preferably recognize and reject introduction of electrochemical biosensors that have already been exposed to user breath.

Figure 2:
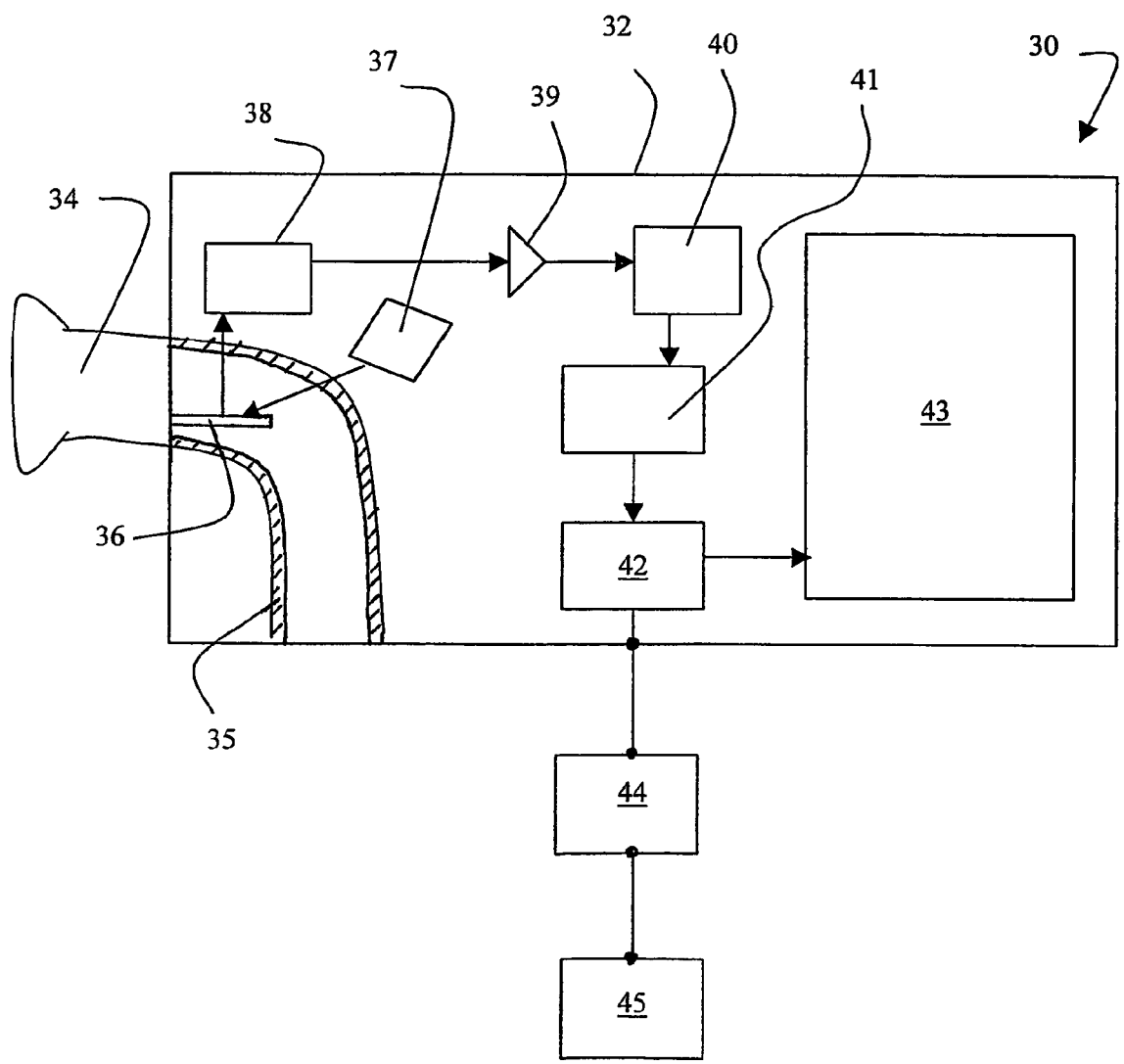
FIG. 2 is a schematic diagram of a hand-held medical apparatus of the present invention incorporating a sensor for the colorimetric detection of acetone in breath.

FIG. 2 depicts an alternate apparatus embodiment 30 of the instant invention. Hand-held medical apparatus 30 comprises housing 32. Apparatus 30 has a disposable/detachable inlet 34 in communication with transparent conduit 35. A disposable enzyme colorimetric biosensor 36 is inserted into the housing 32 and the conduit 35 as shown. A light source 37 is used to direct light onto the biosensor 36. A light detector 38 is used to detect or diffuse light from the biosensor 36. The light detector 38 is in electrical communication with an amplifier 39. The amplifier 39 is in electrical communication with a track and hold circuit 40. The track and hold circuit 40 is in electrical communication with an analog to digital converter 41. A battery, not shown, is used to power the apparatus 30 and, of course, other power sources can be used such as a converter. The analog to digital converter 41 is in electrical communication with a microprocessor 42. The microprocessor 42 is in electrical communication with a liquid crystal display 43 and a first computer 44. The first computer 44 is in communication with a second computer 45 by way of an Internet connection.

A preferred enzyme system used in the biosensor 36 is described in greater detail below and used, for example, with Trinder dye system coupled to horseradish peroxidase. A more general description of the colorimetric enzyme system is disclosed in above referenced U.S. Provisional Patent Application Ser. No. 60/332,349 filed Nov. 9, 2001. Details of suitable electronic circuits and components that can be used herein are described in U.S. Pat. Nos. 4,935,346 and 5,426,032, herein fully incorporated by reference. A mass air sensor system, not shown, can be positioned in the conduit 35 to better assure that a proper volume of user breath has been introduced into the inlet 34 of the apparatus 30. Alternatively, the enzyme system used in the biosensor 36 can be fluorescence based (in which case the light source 37 is the excitation light for the fluorescence) or the enzyme system used in the biosensor 36 can be chemiluminescence based (in which case the light source 37 is not used).

Figure 3:
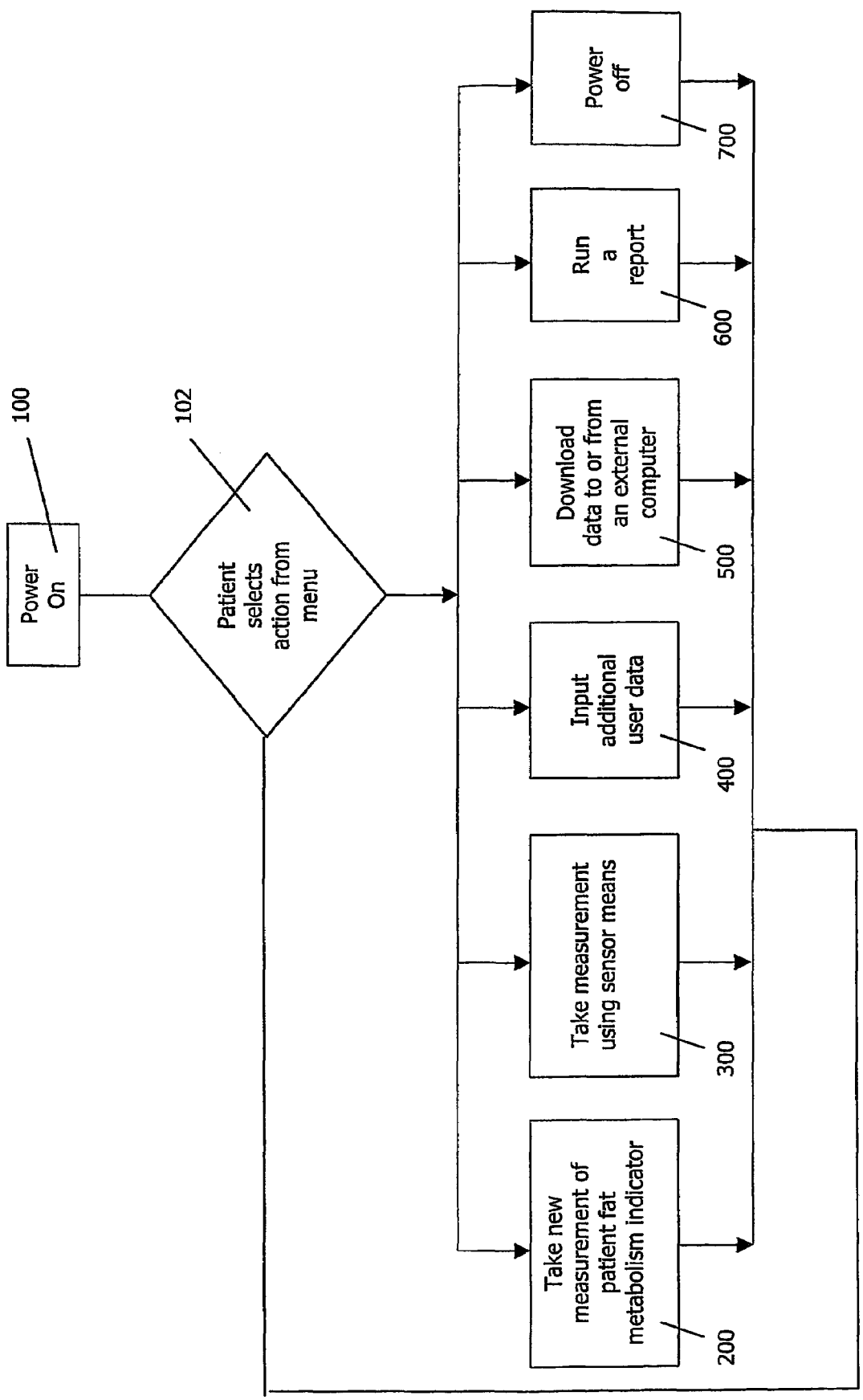
FIG. 3 is a flowchart illustrating one means for the operation of the hand-held medical apparatus of FIG. 1.

FIG. 3 is a flowchart illustrating one means for the operation of medical apparatus 10 of FIG. 1. As shown in FIG. 3, at box 100, the user powers on medical apparatus 10. At box 102, the user selects the desired action from a menu, using user input means. Exemplary desired actions include the actions of boxes 200 (making a new measurement of the user fat metabolism indicator), 300 (making an additional measurement using biosensor 16), 400 (inputting additional data), 500 (downloading data to or from an external computer), 600 (running a report), or 700 (powering medical apparatus 10 off). Upon completion of the selected desired action, the user returns to box 102, for selection of an additional desired action, repeating the process until the session is completed at box 700 by the powering off of medical apparatus 10.

Figure 4:
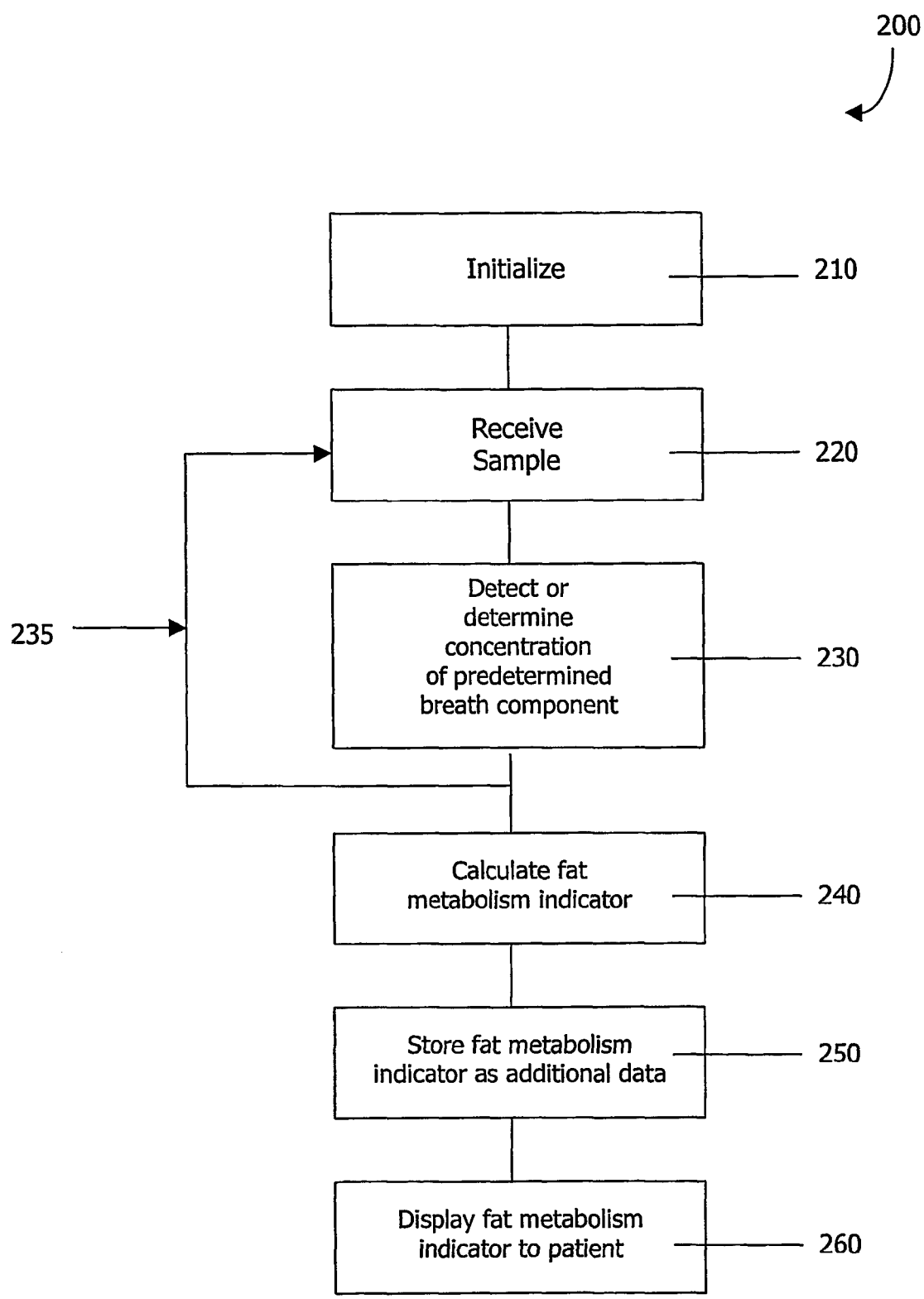
FIG. 4 is a flowchart providing further detail regarding the operation of the hand-held medical apparatus of FIG. 1.

FIG. 4 is a flowchart providing further detail regarding box 200 of FIG. 3 (take a new measurement of the user fat metabolism indicator).

At box 210, the medical apparatus 10 initializes. At box 220, the user is prompted to breathe into the medical apparatus at inlet 14. Box 220 may include means for ascertaining whether the breath sample satisfies pre-determined measurement criteria, and communicating to the user if such pre-determined measurement criteria are not met. Examples of pre-determined measurement criteria include the volume of user breath introduced and the duration of time between the preceding measurement and the present measurement (for instance, if it is desired that the user refrain from making measurements more frequently than at pre-determined intervals).

At box 230, the medical apparatus 10 will determine the concentration of the pre-determined breath component, for instance, acetone, in the sample of user breath. Loop 235 indicates a preferred embodiment, in which additional samples of user breath are introduced (for a predetermined number of times or until the reading stabilizes. In this embodiment, the independent measurements of the predetermined breath component may be averaged (or the stabilized measurement determined) and communicated to box 240 for calculation of the user fat metabolism indicator.

At box 240, the user fat metabolism indicator is calculated. The calculation may involve determining whether or not the concentration of the predetermined breath component falls within a pre-designated range (in which case, the user fat metabolism indicator may be, for instance, "recommended level for safe weight loss", "lower level than recommended level for effective weight loss", or "higher level than recommended for safe weight loss"). In this case, the user fat metabolism indicator is determined by microprocessor 20.

At box 250, the user fat metabolism indicator will preferably be stored in memory.

At box 260, the user fat metabolism indicator will be displayed to the user.

Further detail regarding means by which additional user data is input into medical apparatus 10 or 30 will now be discussed. In addition to measuring a physiologic parameter correlated to a behavior or condition to be changed (for example, breath acetone as a marker for weight loss) and correlating stored patterns of that parameter, information on the psychological or emotional state of the user can be obtained. This information may be either directly obtained from the user or may be inferred from a medical history stored in a computer or both. To acquire information directly, the computer may pose a series of questions to the user. The user may be asked to indicate their perceived state on a scale, for instance. Preferably, the questions are changed from time to time, so that merely routine answers are less likely. Information on the user's emotional or psychological state may also be inferred from the history maintained by the computer. For instance, early enthusiasm for a weight-loss program may be correlated with regular use of the breath analyzer to detect acetone, and a consistent pattern of acetone levels. Discouragement may be indicated by sporadic and increasingly infrequent use of the device, coupled with consistently low levels or fluctuating levels of detected acetone.

The physiologic parameter and the information on the psychological or emotional state of the user are then correlated to select an appropriate response or feedback for the user. For example, adequate levels of acetone in the breath combined with a feeling of general satisfaction may produce a response merely acknowledging that the user is in fact meeting his or her goals. Indications of discouragement coupled with adequate physiologic parameter may require more emphatic positive reinforcement to help the user recognize that he or she is making progress. A depressed emotional state and poor physiologic measurements may require outside intervention. Intervention may include automatically alerting a health care provider or a support person or support group so that personal contact may be made. A connection may be automatically initiated through a communications network as discussed above, for example, telephone or the Internet system, to the health care provider or support person, reporting the probable need for intervention.

The type of feedback provided to the user may also depend on the user's history as recorded by the computer. A process of changing a health-related activity or behavior may be viewed as a project or new job and is characterized by an emotional state which is related to the duration of the project, called herein "an intermediate-term emotional state". Persons undertaking a project generally are observed to be in one of four states or conditions at different times during the project, each state needing a particular type of feed back. A successful project progresses through the four phases. A particular user may take more or less time in a particular phase and may, at times, regress to an earlier state. The four phases may be characterized as a beginning or orientation phase, a dissatisfaction phase, a production or performance phase, and a completion phase. As the project of changing behavior begins, the user is usually enthusiastic, but has little real information relevant to the change in behavior. For example, the user is excited about the prospect of improving health by weight loss, but doesn't know how to prepare appropriate meals in appropriate amounts. In general, specific, detailed direction is needed in this phase and the computer would provide detailed help. Health benefits are not yet apparent to the user.

In the second phase, the health benefits have still not become obvious, and the user may feel discouraged or dissatisfied. This phase needs feedback that is still detailed but which also includes positive re-enforcement to boost morale. In the case of weight loss, the detection of acetone components in the breath can provide immediate positive re-enforcement necessary to help the user through this phase.

In the third phase, physical changes begin to become apparent to the user. The behavior can be seen to be having the desired effect. The user's morale improves and feedback from the system should become less detailed and more supportive. In other words, the user's range of choices increases as the user becomes accustomed to the changed pattern of behavior. Positive re-enforcement is still needed.

In the final phase, the acquired pattern of behavior can be maintained indefinitely. The user's morale and performance are both high. Detailed instructions are not needed and would not contribute to maintaining the desired behavior. Recognition and reward are needed to confirm the successful completion of the changed state. The user maintains the new habits. In the case of weight loss, for example, acetone is a significant breath component only during weight loss, when the body is operating at an energy deficit. When the user is maintaining a particular weight, measurable levels of acetone may not be detected.

The psychological pattern described above generally extends over the duration of an entire project. In the case of sustained weight loss, this period is usually about a year, comprised of six months of actual weight loss and six months of maintenance to allow the body to acclimate to the lower weight. Dieters and other persons trying to change a health-related behavior also experience wide emotional or psychological variation on a short-term basis. The person's need for re-enforcement and support may vary substantially throughout a single day. A recognized phenomenon in diabetics who are trying to lose weight is the tendency to over eat at the end of the day. Emotional states such as boredom, guilt (for eating "forbidden" foods), and lack of emotional support contribute to this phenomenon. By monitoring the user's emotional state throughout the day, additional support or responses can be provided to help the user cope with the short-term variations that can provide a significant barrier to successful behavior modification.

In an especially preferred embodiment of the invention, the sensor will include an enzymatic system. Suitable enzymes which utilize acetone as a substrate include secondary alcohol dehydrogenases, acetone monooxygenases and acetone carboxylases. A more general description of these acetone-specific enzyme systems is disclosed in above referenced U.S. Provisional Patent Application Ser. No. 60/332,349 filed Nov. 9, 2001.

Figure 5:
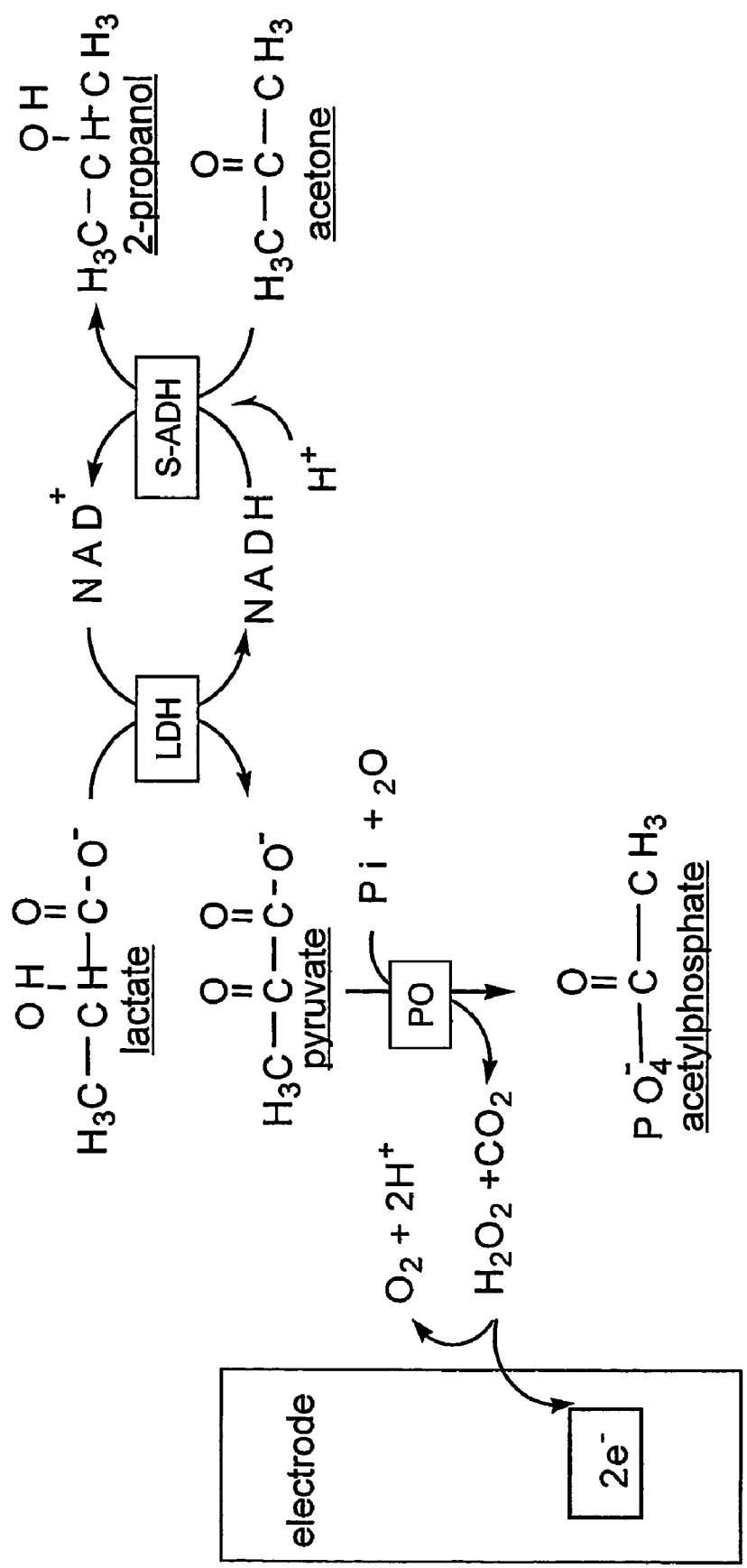
FIG. 5 is a drawing of the reaction pathways of an embodiment of the instant invention using a preferred enzyme that selectively targets acetone as the pre-determined breath component.

Referring now to FIG. 5, one preferred secondary alcohol dehydrogenase (S-ADH) for use in an acetone specific enzyme system is NADH-dependent S-ADH isolated from the Gram-negative soil bacterium *Xanthobacter autotrophicus* strain Py2 (referred to herein as *X. autotrophicus* Py2 or as *X. autotrophicus* st. Py2; ATCC deposit number PTA-4779). This enzyme catalyzes the reduction of acetone in the presence of the reduced pyridine nucleotide cofactor NADH to form 2-propanol and NAD$^+$. Preferably the S-ADH enzyme reaction is coupled to lactate dehydrogenase and pyruvate oxidase enzyme activities so that acetone present in the enzyme system is stoichiometrically converted to $H_2O_2$. $H_2O_2$ is then electrochemically oxidized and detected at the electrode where the anodic current output directly correlates to the concentration of acetone present. Alternatively, horseradish peroxidase may be added in the presence electron donors (chromogenic dye reagents) to allow monitoring of the reaction photometrically.

One preferred acetone monooxygenase for use in an acetone-specific enzyme system is cytochrome P450 acetone monooxygenase, which has been isolated from mice (*Mus musculus*). This monooxygenase has been reported to utilize acetone as a substrate to produce acetol, and is commercially available from PanVera Corporation (Madison, Wis.). See F. Y. Bondoc, et al., Acetone catabolism by cytochrome P450 2E1: Studies with CYP2E1-null mice. *Biochemical Pharmacology*, 58: 461-463 (1999). The enzyme responsible for this activity in bacteria has not yet been fully characterized.

Preferred acetone carboxylases for use in an acetone-specific enzyme system include acetone carboxylase obtained: from *Xanthobacter autotrophicus* strain Py2 (see Sluis, M. K. and Ensign, S. A., Purification and characterization of acetone carboxylase from *Xanthobacter* strain Py2, *PNAS USA*, 94: 8456-8462 (1997)); from *Rhodobacter capsulatus* B10 (see Sluis, M. K. et al., Biochemical, Molecular, and Genetic Analyses of the Acetone Carboxylases from *Xanthobacter autotrophicus* Strain Py2 and *Rhodobacter capsulatus* Strain B10, *J. Bacteriol.*, 184(11), 2969-2977 (2002)); and from *Rhodococcus rhodochrous* B276 (see Clark, D. D. and Ensign, S. A., Evidence for an inducible nucleotide-dependent acetone carboxylase in *Rhodococcus rhodochrous* B276, J. Bact. 181(9): 2752-2758 (1999)). The *Xanthobacter* gene sequences are available in GenBank (accession number AY055852)., and *Rhodobacter capsulatus* B10 genes are available on the website of the "*Rhodobacter Capsulapedia*" sequencing project (See http://rhodol.uchicago.edu). Both the *X. autotrophicus* Py2 and the *R. capsulatus* B10 enzymes are α/β/γ heterotrimers, sharing approximately an 80% overall sequence identity with each other, as well as exhibiting functional identity in catalyzing the same reaction with acetone.

A preferred embodiment of the invention provides a breath acetone diagnostic device having one or more acetone-specific enzyme systems. A preferred use of such a device is in monitoring ketone production in a mammal. Acetone-specific enzyme systems are employed in such a way so that in the presence of acetone, oxidized pyridine nucleotides or hydrogen peroxide are formed as co-products, allowing the reaction be detected electrochemically. These oxidoreductase enzyme systems include, for example: 1) the secondary alcohol dehydrogenase (S-ADH)-catalyzed reduction of acetone with concomitant NAD(P)H consumption; 2) acetone carboxylase reaction coupled to β-hydroxybutyrate dehydrogenase consumption of NAD(P)H; 3) acetone carboxylase reaction ATP hydrolysis coupled to NAD(P)H consumption; 4) S-ADH reaction NAD(P)$^+$ formation coupled to $H_2O_2$ formation; 5) acetone carboxylase reaction ATP hydrolysis coupled to $H_2O_2$ formation; 6) acetone carboxylase reaction coupled to β-hydroxybutyrate dehydrogenase NAD(P)$^+$ formation coupled to $H_2O_2$ formation; 7) acetone monooxygenase coupled to NAD(P)H oxidation; and 8) acetone monooxygenase coupled to coupled to $H_2O_2$ formation. In all of these enzyme systems, the pyridine nucleotide or hydrogen peroxide is detectable electrochemically. Of course, other detection means known in the art (such as colorimetry, fluorescence, chemiluminescence and calorimetry) can also be utilized.

With regard to some of the terms used herein, NAD(P)$^+$ is used herein to mean "either or both of NAD$^+$ (nicotinamide adenine dinucleotide, oxidized form) and NADP$^+$ (nicotinamide adenine dinucleotide phosphate, oxidized form)." NAD(P)H is used herein to mean "either or both of NADH (nicotinamide adenine dinucleotide, reduced form) and NADPH (nicotinamide adenine dinucleotide phosphate, reduced form)." Nicotinamide adenine dinucleotide is also called 3-carbamoyl-1-—D-ribofuranosyl-pyridinium hydroxide 5'-ester with adenosine 5'-pyrophosphate, inner salt. Nicotinamide adenine dinucleotide phosphate is also called 3-carbamoyl-1-—D-ribofuranosyl-pyridinium hydroxide 5'→5'-ester with adenosine 2'-(dihydrogenphosphate) 5'-(trihydrogen pyrophosphate), inner salt. As used herein, "$A_{NNN}$" indicates "absorbance measured at NNN nanometers wavelength." As used herein, "$_{NNN}$" indicates "extinction coefficient measured at NNN nanometers wavelength."

"Enzyme" as used herein means "catalytically functional biomolecule;" thus any biomolecule that can perform a named catalytic function as its primary catalytic activity is considered an enzyme of that name, regardless of other considerations such as origin, native or engineered structure, size, etc.

"Platinized carbon," as used herein, indicates platinum-coated carbon, for example at least partially platinum-coated carbon nanoparticles.

"Photometric," as used herein, indicates any detection mode in which photons are utilized and includes, but is not limited to, colorimetric, spectrometric, spectrophotometric, luminescence-based, chemiluminescence-based, electrogenerated chemiluminescence-based, bioluminescence-based, and fluorescence-based methods.

In order to address certain difficulties associated with subject health maintenance, an enzyme-based biosensor has been developed, which enables the coupling of enzyme-mediated metabolism of acetone to electrochemically detectable signals produced via one or more of the signal mediators. Any acetone-specific enzyme capable of linkage to an electrochemically detectable co-factor or by-product may be suitable for the enzyme system of the invention. In a preferred embodiment, an electrochemical biosensor for detecting acetone in a biological sample contains at least one acetone-specific enzyme system, and a means for detecting a product resulting from a reaction between the at least one acetone-specific enzyme system and acetone in the biological sample. The detection means may be either electrochemical or non-electrochemical.

Acetone-Specific Enzymes

A number of enzymes, mainly from bacterial sources, have been described which specifically utilize acetone as a substrate. These enzymes have been obtained from and/or characterized in aerobic and anaerobic bacteria that are able to grow using acetone as a sole carbon and energy source.

Acetone may be formed in bacteria by the action of secondary alcohol dehydrogenase (S-ADH), an enzyme that operates in conjunction with one of two different acetone metabolic pathways: an $O_2$-dependent (oxygen utilizing) pathway in which the acetone is then oxidized to produce acetol, and a $CO_2$-dependent (carbon dioxide utilizing) pathway in which the acetone is then converted to acetoacetate. The acetone formation reaction catalyzed by S-ADH is freely reversible and normally requires a coenzyme that is typically either NAD(H) or NADP(H). The reduction of acetone to isopropanol by oxidation of NAD(P)H (the reverse, S-ADH-catalyzed reaction) involves redox chemistry by which acetone concentration can be monitored (for example, by means of electrochemical determination of NAD(P)H consumption). A variety of secondary alcohol dehydrogenases have been purified and characterized. Those best studied are S-ADHs obtained from hydrocarbon oxidizing (that is propane utilizing) bacteria, which employ $O_2$-dependent acetone metabolic pathways. S-ADH enzymes have also been isolated from or described in microorganisms not associated with hydrocarbon oxidation (that is propane degradative metabolism). These include methylotrophic bacteria and yeast, methanogenic Archaea, and fermentative anaerobes. Of these enzymes, S-ADH from *Thermoanaerobium brockii* is commercially available as a heat-treated crude preparation or in purified form (available from Sigma Chemical Co., St. Louis, Mo.). This enzyme is well characterized and is an NADPH-specific dehydrogenase.

In some propane-oxidizing bacteria, acetone is formed as an intermediate that is then understood to undergo hydroxylation in an $O_2$-dependent mono-oxygenase-catalyzed reaction to form acetol (hydroxyacetone). Acetol is then further oxidized to methylglyoxal catalyzed by an acetol dehydrogenase, or is involved in a carbon-carbon cleavage reaction producing C1 and C2 fragments. Acetone mono-oxygenase, which is a pyridine nucleotide-dependent enzyme, provides the necessary requirements for electrochemical detection in an acetone biosensor (as described above). Acetone metabolism via acetol as an intermediate has been identified in in vivo studies of acetone-utilizing bacteria. Also, P450 monooxygenases have been identified in mammals as using an identical mechanism (to oxidize acetone to acetol). An acetone mono-oxygenase suitable for use in an acetone-specific enzyme system is a cytochrome P450 acetone mono-oxygenase isolated from mice (*Mus musculus*). This monooxygenase has been reported as utilizing acetone as a substrate to produce acetol, and is commercially available from PanVera Corporation (Madison, Wis.). See F. Y. Bondoc et al., Acetone catabolism by cytochrome P450 2E1: Studies with CYP2E1-null mice. *Biochemical Pharmacology*, 58: 461-63 (1999). The enzyme responsible for this activity in bacteria has not yet been fully characterized. In addition, acetone mono-oxgenase can be coupled to $H_2O_2$ generation by including a galactose oxidase in the enzyme system; galactose oxidase oxidizes acetol to form $H_2O_2$ which can be detected either electrochemically or non-electrochemically.

Mammalian P450 cytochromes containing acetone mono-oxygenase activity and P450 reductase may be prepared from heptatic microsomes. P450 acetone mono-oxygenase catalyzes the following hydroxylation reaction:

$$NAD(P)H + H^+ + acetone + O_2 \rightarrow NAD(P)^+ + acetol + H_2O$$
(P450 acetone mono-oxygenase)

P450 monooxygenases are typically comprised of two enzyme components including a pyridine nucleotide-dependent reductase and an active site-containing oxygenase component. NAD(P)H provides the necessary reductant for $O_2$ activation and incorporation of one oxygen atom into the aliphatic hydrocarbon substrate. With some P-450 monooxygenases, a third electron transfer component, cytochrome $b_5$, will stimulate activity. Acetone-dependent consumption of NAD(P)H by an acetone mono-oxygenase reaction could be monitored electrochemically as described below for secondary alcohol dehydrogenase-coupled and acetone carboxylase-coupled enzyme systems, as shown in FIG. 1. Alternatively, the reaction could be monitored by following $O_2$ consumption electrochemically, or monitored optically by measuring absorbance or fluorescence of NAD(P)H consumption as described below.

For other bacteria, including both aerobes and anaerobes, acetone metabolism is has been identified as proceeding by a $CO_2$-dependent carboxylation reaction producing acetoacetate. Acetone carboxylase, the enzyme that catalyzes this reaction, has recently been purified to homogeneity from two bacterial sources. Although acetone carboxylase does not catalyze a reaction that is readily detectable electrochemically, this enzyme has high specificity for acetone and, according to the present invention, can be coupled with other enzymes that catalyze redox reactions (for example dehydrogenases, oxidases). The feasibility of using coupling enzymes with acetone carboxylase for electrochemical detection had not been reported prior to this disclosure.

Suitable acetone carboxylases for use in an acetone-specific enzyme system include, but are not limited to, acetone carboxylase obtained: from *Xanthobacter autotrophicus* strain Py2 (referred to herein as *X. autotrophicus* Py2 or as *X. autotrophicus* st. Py2) (see Sluis, M. K. and Ensign, S. A., Purification and characterization of acetone carboxylase from *Xanthobacter* strain Py2, *PNAS USA,* 94: 8456-8462 (1997)); from *Rhodobacter capsulatus* B10 (see Sluis, M. K. et al., Biochemical, Molecular, and Genetic Analyses of the Acetone Carboxylases from *Xanthobacter autotrophicus* Strain Py2 and *Rhodobacter capsulatus* Strain B10, *J. Bacteriol.*, 184(11):2969-77 (2002)); and from *Rhodococcus rhodochrous* B276 (see Clark, D. D. and Ensign, S. A., Evidence for an inducible nucleotide-dependent acetone carboxylase in *Rhodococcus rhodochrous* B276, *J. Bact.* 181(9):2752-58 (1999)). *Xanthobacter autotrophicus* strain Py2 was deposited in the American Type Culture Collection (ATCC) on Oct. 29, 2002 under ATCC Accession No. PTA-4779. The ATCC is located at 10801 University Boulevard, Manassas, Va. 20110-2209 U.S.A. and may be contacted at P.O. Box 1549, Manassas, Va. 20108 U.S.A. This deposit was made in accordance with the requirements of the Budapest Treaty. The amino acid sequences of the subunits of the *X. autotrophicus* Py2 acetone carboxylase are set forth in SEQ ID NOs:1, 2, and 3; the nucleotide sequences of the genes encoding these subunits are available in GenBank (See accession number AY055852). The amino acid sequences of the *Rhodobacter capsulatus* B10 acetone carboxylase gene are set forth in SEQ ID NOs:4, 5, and 6; the nucleotide sequences of the genes encoding these subunits are available on the website of the "*Rhodobacter Capsulapedia*" sequencing project (See http://rhodol.uchicago.edu). Both the *X. autotrophicus* Py2 and the *R. capsulatus* B10 acetone carboxylase enzymes are alpha/beta/gamma (α/β/γ) heterotrimers, sharing approximately an 80% overall sequence identity with each other, as well as exhibiting functional identity in catalyzing the same reaction with acetone.

Acetone-Specific Enzyme Systems

In a preferred embodiment of the invention, a breath acetone diagnostic device is provided that contains one or more acetone-specific enzyme systems. A preferred use of such a device is in monitoring ketone production in a mammal. In developing the invention, a number of oxidoreductase enzyme systems were investigated that, in the presence of acetone, oxidized pyridine nucleotides as cofactors or produced hydrogen peroxide as a co-product, allowing the reaction be detected electrochemically. These oxidoreductase enzyme systems include, for example: 1) the secondary alcohol dehydrogenase (S-ADH)-catalyzed reduction of acetone with concomitant NADPH consumption; 2) S-ADH-catalyzed reduction of acetone with concomitant NADH consumption; 3) acetone carboxylase reaction coupled to β-hydroxybutyrate dehydrogenase consumption of NADPH; 4) acetone carboxylase reaction coupled to β-hydroxybutyrate dehydrogenase consumption of NADH; 5) acetone carboxylase reaction ATP hydrolysis coupled to NADPH consumption; 6) acetone carboxylase reaction ATP hydrolysis coupled to NADH consumption; 7) S-ADH reaction $NADP^+$ formation coupled to $H_2O_2$ formation; 8) S-ADH reaction $NAD^+$ formation coupled to $H_2O_2$ formation; 9) acetone carboxylase reaction ATP hydrolysis coupled to $H_2O_2$ formation; 10) acetone carboxylase reaction coupled to β-hydroxybutyrate dehydrogenase $NADP^+$ formation coupled to $H_2O_2$ formation; 11) acetone carboxylase reaction coupled to β-hydroxybutyrate dehydrogenase $NAD^+$ formation coupled to $H_2O_2$ formation; 12) acetone mono-oxygenase coupled to NADPH oxidation; 13) acetone mono-oxygenase coupled to NADH oxidation; 14) acetone mono-oxygenase coupled to $H_2O_2$ formation; and 15) acetone monooxygenase-catalyzed NAD(P)+ formation coupled to $H_2O_2$ formation.

In all of these enzyme systems, the pyridine nucleotide or hydrogen peroxide is detectable electrochemically, though other detection means known in the art can be utilized.

The use of enzymes as bioactive interfaces is well known in the art, and such interfaces are used in analytical methods of detecting electronic transduction of enzyme-substrate reactions. Direct electrical activation of enzymes such as redox enzymes permits stimulation of bioelectrocatalyzed oxidation or reduction of enzyme substrates. Rapid transfer of electrons between an electrode and a given redox enzyme results in current generation corresponding to the rate of turnover of the electron exchange between the substrate and biocatalyst. In other words, the transduced current of the system correlates with enzyme substrate concentration. Electrical contacting of redox proteins in a biosensor and the electrode support contained therein may be mediated by direct electron transfer with electrode surfaces. Redox enzymes lacking direct electrical communication with electrodes may achieve electrical contact by mediated electron transfer via active charge carriers. An electron relay may be oxidized or reduced at an electrode surface, and diffusion of the oxidized or reduced relay into enzyme results in short electron transfer distances with respect to the active redox center for mediated electron transfer and, thus, electrical activation of a biocatalyst.

Detection Means

The acetone-selective enzyme system, in acting upon the acetone substrate, generates an electrochemically or non-electrochemically detectable product or by-product directly, or the enzyme system will also include at least one further component. The further component may be: one or more additional enzyme(s) forming an enzymatic pathway utilizing the product or by-product of the initial enzymatic acetone reaction to thereby generate a photometrically or electrochemically detectable product or by-product; or at least one signal mediator; or both the additional enzyme(s) and the signal mediator(s). The signal mediator(s) may be selected from, for example: indicators, such as a pH-change indicators; electron transfer mediators; photometric mediators, and other components.

In an electrochemical embodiment of the invention, an acetone-specific redox enzyme or enzyme system is selected that utilizes an electrochemically detectable cofactor, such as NADH, or generates a by-product, such as $H_2O_2$, during the course of the enzymatic reaction. These enzyme systems can selectively detect acetone in biological samples, such as breath or biological fluids. However, detection of acetone is not limited to electrochemical means, and the enzyme system of this invention may be used in other types of devices, for example devices employing known V, fluorescence, or other suitable methods of detecting acetone-specific enzyme-substrate interactions.

Non-Electrochemical Detection Means

Non-electrochemical detection involves, for example, any calorimetric or photometric detection mode known in the art (for example, any colorimetric, spectrometric, spectrophotometric, luminescence-based, chemiluminescence-based, or fluorescence-based detection method.)

A fluorescence detection device has the following minimum requirements: it must be light-tight to eliminate stray light from its surroundings, its fluors must be stored in the dark to prevent photobleaching (that is increase shelf life), and its optics must be at a 90° angle. A diode emitting the desired excitation wavelength can function as the light source, and a PMT can function as the detector. These need not be elaborate since both the excitation and emission max of the fluor are known, and these are the only wavelengths required. The same breath collection and acetone partitioning apparatus used in an enzyme electrochemical device can be used in a fluorescence device. A portable fluorescence detector for aflatoxin has been described in the literature (M A Carlson et al., An automated handheld biosensor for aflatoxin, *Biosens. Bioelectr.* 14:841 (2000)), so a precedent for a portable fluorescence detector exists.

Both direct and indirect fluorescence allows the detection of acetone from both breath and body fluids. The acetone-specific enzymes and their cofactors can be immobilized on a disposable strip using conventional entrapment techniques. When acetone diffuses through the immobilization medium to the enzyme, the acetone will be chemically altered. Unfortunately, acetone itself is not fluorescent and cannot be derivatized inside the detection device. Thus another reagent needs to be derivatized with a fluorophore or a fluor needs to be added to the system to monitor the reaction. For the secondary alcohol dehydrogenase system, NADH consumption can be monitored, while the acetone carboxylase system can use ATP-analogs. As the NADH or ATP-analog is consumed, fluorescence intensity should decrease. Since the reaction with acetone is stoichiometric, fluorescence intensity is proportional to acetone concentration. The $H_2O_2$-generating systems can use $H_2O_2$ and an additional fluor. In these systems, $H_2O_2$ production causes an increase in fluorescence intensity that is proportional to acetone concentration.

We have verified that NADH in 100 mM phosphate buffer, pH 7.6, emits light directly at approximately 470 nm when excited with 342 nm light; these data agree with those reported in the literature (M A Carlson et al., 2000). In addition, NADH direct fluorescence has a 0.1-10 μM linear working range, is independent of pH from pH 6-13, decreases in intensity 1.6% per °C., and exhibits little altered fluorescence intensity in the presence of cations and enzymes below pH 10 (See P W Carr & L D Bowers, Immobilized Enzymes in Analytical and Clinical Chemistry, In *Chemical Analysis. A Series of Monographs on Analytical Chemistry and Its Applications* (P J Elving & J D Winefordner, eds.; vol. 56, p. 122 (Wiley-Interscience, New York, 1980), and references contained therein). Several groups have described the use of direct NADH fluorescence to monitor enzymatic activity (A K Williams & J T Hupp, Sol-gel encapsulated alcohol dehydrogenase as a versatile, environmentally stabilized sensor for alcohols and aldehydes, *J. Am. Chem. Soc.* 1998, 120:4366; and V P Iordanov et al., Silicon thin-film UV filter for NADH fluorescence analysis, *Sens. Actuat. A*, 2002, 97-98:161).

Indirect fluorescence of NADH can be detected using the dye rhodamine 123. Non-radiative energy transfer (also called fluorescence resonance energy transfer, FRET) occurs between the excited states of NADH and rhodamine 123. FRET is a well-known technique for determining the proximity of two species, i.e. FRET is utilized as a "molecular yardstick" both in vitro and in vivo. In this context of an acetone-specific enzyme system, a donor fluorophore, e.g., NADH, transfers its excited state energies to the acceptor fluorophore, rhodamine 123. (R P Haugland, *Handbook of Fluorescent Probes and Research Products*, 2002 (9$^{th}$ ed.; Molecular Probes, Inc.; Eugene, Oreg.); K Van Dyke et al., eds. *Luminescence Biotechnology. Instruments and Applications*, 2002 (CRC Press; Boca Raton, Fla.) and references contained therein). The NADH-rhodamine 123 FRET method has been successfully employed in other enzymatic assays (M H Gschwend et al., Optical detection of mitochondrial NADH content in intact human myotubes, *Cell. Mol. Biol.* 47:OL95 (2001); H. Schneckenberger et al., Time-gated microscopic imaging and spectroscopy in medical diagnosis and photobiology, *Opt. Eng.* 33:2600 (1994)). Bioluminescence resonance energy transfer, or BRET, may also be used in conjunction with an acetone-specific enzyme system according to the present invention. In BRET, the donor fluorophore is replaced by a luciferase. Bioluminescence from luciferase in the presence of a substrate excites the acceptor fluorophore. BRET has also been applied in vitro and in vivo (K Van Dyke et al., 2002).

ATP can be derivatized with a fluorophore for indirect fluorescence. Several commercially available dyes include BODIPY ATP and trinitrophenyl ATP (Haugland, 2002). These analogs change their fluorescence intensity or become fluorescent when bound to an enzyme's ATP binding site.

Indirect fluorescence detection of $H_2O_2$ has also been reported (Carr & Bowers, 1980). These methods utilize dyes that reduce the peroxide to $H_2O$ and are themselves oxidized. Homovanillic acid (4-hydroxy-3-phenylacetic acid) and p-hydroxyphenylacetic acid are among the most commonly used in clinical chemistry (Carr and Bowers, 1980). A commercially available kit uses the dye Amplex Red for fluorescence detection of $H_2O_2$ (Haugland, 2002).

Any fluorescent dyes and fluorescence-detectable enzyme substrate or cofactor analogs can be used in a fluorescence device to detect acetone in breath or bodily fluids.

Chemiluminescence (CL) and electrogenerated chemiluminescence (ECL) (collectively referred to herein as "(E)CL") are widely used in medical diagnostics and analytical chemistry (C Dodeigne et al., Chemiluminescence as a diagnostic tool: A review, *Talanta* 2000, 51:415; K A Fähnrich et al., Recent applications of electrogenerated chemiluminescence in chemical analysis, *Talanta* 2001, 54:531). Enzyme-based (E)CL systems are sensitive and specific, and many CL systems are used with enzyme cycling to detect $H_2O_2$ (Dodeigne et al., 2000). (E)CL can detect picomolar (pM; $10^{-12}$ M) concentrations of analyte over a wide linear range (Dodeigne et al., 2000; Fähnrich et al., 2001). An (E)CL device can be constructed in accordance with the following principles. Since the reaction itself emits light, an (E)CL device does not need a light source. A photomultiplier tube (PMT) can function as the detector; (E)CL is visible to the unaided, dark-adapted eye. A battery can be the power source for ECL. ECL requires electrodes and a source of applied potential. Like a fluorescence detection device, (E)CL devices need to be light tight and their reagents need to be protected from light until use. Also like fluorescence, (E)CL requires derivatized reagents or additional enzymes and reagents to detect acetone. (E)CL devices can be used with disposable strips (B D Leca et al., Screen-printed electrodes as disposable or reusable optical devices for luminol electrochemiluminescence, *Sens. Actuat. B*. 2001, 74: 190) and can be miniaturized (Y Lv et al., Chemiluminescence biosensor chip based on a microreactor using carrier airflow for determination of uric acid in human serum, *Analyst* 2002, 127:1176). An optical electrode (or optrode) can be fabricated using an acetone-specific enzyme system according to the present invention. For example, an optrode such as that used in a glucose optrode that uses ECL, may be employed (see C H Wang et al., Co-immobilization of polymeric luminol, iron(II) tris(5-aminophenanthroline) and glucose oxidase at an electrode surface, and its application as a glucose optrode, *Analyst* 2002, 127:1507)).

The most common CL systems involve the detection of $H_2O_2$ or another reactive oxygen species (Carr & Bowers, 1980; Haugland, 2002; Dodeigne et al., 2000; K Van Dyke et al., 2002) and references contained therein). The classic system is luminol-peroxidase. In basic solution, $H_2O_2$ oxidizes luminol to an excited amino-phthalate ion; the excited amino-phthalate ion emits a 425-nm photon to return to its ground state. When used in medical diagnostics, this reaction is catalyzed with horseradish peroxidase (HRP) (Carr & Bowers, 1980; Dodeigne et al., 2000). Thus any enzyme system that produces $H_2O_2$ or requires a cofactor that can react with additional reagents to form $H_2O_2$ can be used in a CL device. The $H_2O_2$-generating systems described herein can use luminol-HRP directly for acetone detection. These enzyme cycling schemes increase the light emission over time because the substrates are continuously recycled (Dodeigne et al., 2000). While luminol itself is frequently used in CL, its improved analogs can also be used in a CL-based detector according to the present invention, in place of luminol, in order to increase the sensitivity. Examples of such analogs are those described in Carr & Bowers, 1980; and Dodeigne et al., 2000.

NADH detection using CL is a common technique (Dodeigne et al., 2000). For example, in the presence of 1-methoxy-5-methylphenazinium methylsulfate, NADH reduces $O_2$ to $H_2O_2$ which generates light using the luminol-peroxidase system (Dodeigne et al., 2000). For an acetone monitor, the $O_2$ in ambient air is sufficient to detect acetone using this system. NADH also reacts with oxidized methylene blue to form $H_2O_2$ that reacts with luminol (Carr and Bowers, 1980). NADH can also act as a CL quencher. The fluorescence intensity of the substrate ALPDO is decreased in the presence of NADH and HRP (Van Dyke et al., 2002). NADH also can be used with $Ru(bpy)_3^{2+}$ for ECL (E S Jin et al., An electrogenerated chemiluminescence imaging fiber electrode chemical sensor for NADH, *Electroanal*, 2001, 13(15):1287). Rhodamine B isothiocyanate can also be used for ECL detection of $H_2O_2$ (Fähnrich et al., 2001). ECL also offers another advantage in that, by use of a properly poised electrode, the electroactive species can be regenerated at the electrode surface. Regeneration both conserves reagents and allows durable and/or "reagentless' sensors. All these systems can be used in a (E)CL device interfaced to an acetone-specific enzyme system according to the present invention.

CL is widely used to quantitate ATP simply and sensitively (Carr & Bowers, 1980). The enzyme luciferase catalyzes the reaction of ATP and luciferin to produce excited-state oxyluciferin, which returns to its ground state with the emission of a 562-nm photon (Carr & Bowers, 1980; Haugland, 2002). The quantum yield for this reaction is very high; $10^{-14}$ mol ATP can be detected. A kit for this reaction is commercially available (Haugland, 2002). Because luciferase is the enzyme that causes fireflies to "glow," this reaction is referred to as bioluminescence. Both native and recombinant luciferase are commercially available, and several groups have reported using bioluminescence ATP assays to quantify biological analytes (P Willemsen et al., Use of specific bioluminescence cell lines for the detection of steroid hormone [ant]agonists in meat producing animals, *Anal. Chim. Acta* 2002, 473:119; S J Dexter et al., Development of a bioluminescent ATP assay to quantify mammalian and bacterial cell number from a mixed population, *Biomat.* 2003, 24:nb27). In addition to the luminol-HRP system, $H_2O_2$ can also be detected using peroxyoxalic acid derivatives (Dodeigne et al., 2000). $H_2O_2$ can also be detected with CL non-enzymatically with ferricyanide as the catalyst (Dodeigne et al., 2000). In these (E)CL systems, the acetone-specific enzymes described herein either produce $H_2O_2$ or require cofactors that can be utilized to form $H_2O_2$.

Optical biosensors use photometric detection (that is, absorbance, fluorescence) of substrates consumed or products formed by the reaction catalyzed by the enzyme system incorporated into the sensor. The acetone-specific enzyme reactions described may be monitored by several photometric methods-namely by measuring NAD(P)H absorbance at 340 nm for the pyridine nucleotide-dependent enzymes or absorbance of the quinoneimine dye for the $H_2O_2$ forming enzyme systems. For the later, addition of a peroxidase allows detection of $H_2O_2$ by catalyzing the reduction of $H_2O_2$ with concomitant oxidation of a dye compound that upon oxidation absorbs at a specified wavelength. Peroxidase enzymes (for example, commercially available horseradish peroxidase) typically have broad substrate specificities so several different electron donor compounds may be used. NAD(P)H consumption may also be measured by fluorescence detection (excitation at 350 nm and emission at 450 nm).

Calorimetry may be employed as a detection means in an acetone-specific sensor according to the present invention. Chemical reactions are typically either exo- or endothermic; that is, they release or absorb heat as they occur. Calorimeters detect and measure this heat by measuring a change in the temperature of the reaction medium (K Ramanathan & B Danielsson, Principles and applications of thermal biosensors, Biosens Bioelectr. 16:417 (2001); B Danielsson, Enzyme Thermistor Devices. In *Biosensor Principles and Applications*. Vol. 15, pp. 83-105 (L J Blum & P R Coulet, eds.; Bioprocess Technology Series, volume 15; Marcel Dekker, Inc: New York, 1991, pp. 83-105, and references contained therein). Thus, the action of an acetone-specific enzyme or enzyme system may be monitored calorimetrically. Calorimeters have been designed that are sensitive enough to detect protein conformational changes, and calorimetry has been used to study many enzymatic reactions in detail (M. J. Todd & J Gomez, Enzyme kinetics determined using calorimetry: a general assay for enzyme activity? Anal. Biochem. 2001, 296:179 (2001)).

The major advantage of calorimetry is the lack of derivatization required for analysis (Danielsson, 1991). Since most reactions involve heat exchange, and this heat is detected, no chromophores, fluorophores, luminophores, "mediators," or other modifications of the analyte are required. Reagents and analytes can be used "as is." This allows the analysis of both reactions that lack a chromophore or fluorophore and/or would be difficult or impossible to derivatize or couple to the generation of an electroactive species.

Miniaturized or chip-based thermosensors have been reported in the literature (Ramanathan & Danielsson, 2001; B Xie & B Danielsson, Development of a thermal microbiosensor fabricated on a silicon chip. Sens. Actuat. B 6:127 (1992); P Bataillard et al., An integrated silicon thermopile as biosensor for the thermal monitoring of glucose, urea, and penicillin. Biosen. Bioelect. 8:89 (1993)). These devices range from radically arranged thermopiles on freestanding membranes to groups of thermopiles constructed on silicon/glass microchannels. These devices have been used to detect specific, single enzymatic reactions (Danielsson, 1991; Xie & Danielsson, 1992; Bataillard et al., 1993). Moreover, two groups have reported thermosensors for glucose (B Xie et al., Fast determination of whole blood glucose with a calorimetric micro-biosensor, Sens. Actuat. B 15-16:141 (1993); M J Muehlbauer et al., Model for a thermoelectric enzyme glucose sensor, Anal. Chem. 61:77 (1989); B C Towe & E J Guilbeau, Designing Medical Devices, 1998, http://lsvl.la.asu.edu/asubiotech/slideshow/slide19.html (accessed January 2002). Preliminary experiments using a conventional calorimeter indicate that the secondary alcohol dehydrogenase-acetone reaction is exothermic (data not shown).

For the acetone monitor described herein, the acetone-specific enzymes and their cofactors can be immobilized on a thermopile via conventional entrapment methods. The enzymes and reagents associated with the coupled electrochemical detection, electrochemical mediators, and "photonic" mediators (luminophores) are unnecessary for calorimetry. The reaction involving acetone can be monitored directly without modification or derivatization. When acetone in the breath or fluid sample diffuses through the immobilization medium and encounters the enzyme, the acetone will be chemically altered. This reaction will generate or absorb heat, causing a temperature change. Comparison of this temperature with that of a reference thermopile will quantify this heat; the measurement is differential. The quantity of heat released or absorbed is proportional to the analyte concentration.

For breath collection, partitioning the acetone from the gas phase to the liquid phase, that is, condensation, is exothermic. The reference or dual thermopile can compensate for this heat. Thus an enzyme calorimetric acetone monitor can use the same breath collection apparatus as an enzyme electrochemical acetone monitor except for the addition of the dual thermopile.

The entire enzyme calorimetric device needs to be sufficiently insulated to prevent heat exchange with its surroundings. Except for electrochemical detection, other aspects of the device, such as enzyme stability, specificity, device portability, etc., described in this document are the same as those for an enzyme electrochemical device.

Thus, useful methods for achieving signal transduction in biosensors according to the present invention include not only electrochemical (amperometric or potentiometric), but also optical or photometric (including colorimetry, fluorescence-based techniques, or chemiluminescence-based techniques), and calorimetric means, all of which are useful in application to acetone biosensor signal transduction.

Therefore, although electrochemical detection means are described and exemplified in detail herein, the enzyme systems of the invention are not limited to use in biosensors employing electrochemical detecting strategies. Other detection strategies may be suitably integrated into a biosensor specific for acetone in biological samples. Photometric assays, such as assays in which changes in the amount of light absorbed in a reaction solution over time may be used. Likewise, assays in which changes in fluorescence or changes in sample turbidity may be employed for detecting acetone-specific enzyme-substrate interactions. Such photometric assays are discussed hereinbelow. Redox potentials of $H_2O_2$ and colorimetric/photometric detection of coenzymes is discussed by Bergmeyer. Photometric assays for enzymatic activity are generally described by John in "Photometric Assays". An NADH-consumption measuring electrode is disclosed by Hart et al. in a 1999 article published in Electroanalysis. Vanysek discloses redox potentials in general, and oxidation-reduction potentials of various compounds suitable for use in biochemical applications are disclosed by Voet & Voet.

An enzyme system employing S-ADH coupled to alanine dehydrogenase was successfully monitored spectrophotometrically for NADH formation. In addition, since the reaction also generates ammonium ion, an optical sensor for $NH_4^+$ can be employed as the detection means for such an enzyme system. One such optical means is described by T D Rhines and M A Arnold, Fiber-optic biosensor for urea based on sensing of ammonia gas, *Anal Chim. Acta,* 1989, 227: 387; several enzyme-based amperometric $NH_4^+$ sensors are commercially available. For acetone detection, ammonia production can be coupled to the secondary alcohol dehydrogenase system as above; ammonia concentration would then be proportional to acetone concentration. Another enzyme scheme to couple acetone to ammonia production is the following:

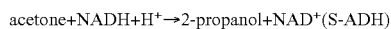
acetone+NADH+H$^+$→2-propanol+NAD$^+$(S-ADH)

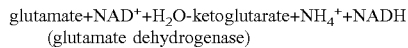
glutamate+NAD$^+$+H$_2$O-ketoglutarate+NH$_4^+$+NADH
(glutamate dehydrogenase)

This second scheme can be used either optically or amperometrically to detect acetone. Additionally, the NADH is recycled. Likewise, an enzyme system in which acetone carboxylase is coupled to glutamate dehydrogenase, generates $NH_4^+$ and so can be detected optically or amperometrically and correlated with acetone concentration.

Electrochemical Detection Means

Amperometric biosensors work by generating current between two electrodes by enzymatically producing or consuming a redox-active compound. Several examples of amperometric acetone biosensor schemes have been described in which NAD(P)H or $H_2O_2$ are consumed or generated enzymatically in response to the presence of acetone. In examples where the transducer is $H_2O_2$, an alternative means to monitor the reaction amperometrically could be to employ a Clark-type oxygen electrode and measure a decrease in $O_2$ concentration. For example, in the case for the secondary alcohol dehydrogenase (S-ADH) coupled to $H_2O_2$ formation, the enzyme system catalyzes the following:

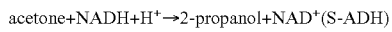
acetone+NADH+H$^+$→2-propanol+NAD$^+$(S-ADH)

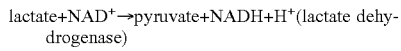
lactate+NAD$^+$→pyruvate+NADH+H$^+$(lactate dehydrogenase)

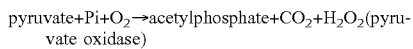
pyruvate+Pi+O$_2$→acetylphosphate+CO$_2$+H$_2$O$_2$(pyruvate oxidase)

Oxygen is then reduced/consumed at the cathode generating a concentration gradient between the electrode and the bulk solution. The rate of electrochemical reaction is dependent on the oxygen concentration in solution.

Potentiometric biosensors employ ion-selective electrodes in which the release or consumption of ions during an enzyme reaction is measured (for example, H$^+$, CN$^-$, NH$_4^+$) (1, 2, 3). For example, a potentiometric biosensor for measuring acetone concentration can be utilized where $NH_4^+$ formation is coupled to the reaction catalyzed by S-ADH and alanine dehydrogenase as follows:

acetone+NADH+H$^+$→2-propanol+NAD$^+$(S-ADH)

alanine+NAD$^+$→pyruvate+NADH+H$^+$+NH$_4^+$(alanine dehydrogenase)

(Photometric data for this system has already been obtained to verify its utility for acetone-specific signal transduction: see the discussion under the "Results" section, below).

A very similar system can be utilized with acetone carboxylase ("β-OH-butyrate dehydr." being "beta-hydroxbutyrate dehydrogenase"):

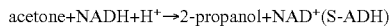
acetone+ATP+CO$_2$→acetoacetate+AMP+2P$_i$(acetone carboxylase)

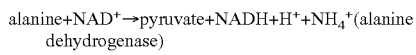
acetoacetate+NADH+H$^+$→β-hydroxybutyrate+NAD$^+$
(β-OH-butyrate dehydr.)

alanine+NAD$^+$→pyruvate+NADH+H$^+$+NH$_4^+$(alanine dehydrogenase)

Another type of electrochemical biosensor that may be employed is a light-addressable potentiometric sensor. In one embodiment of such a device, the acetone-specific enzyme system(s) may be applied to (e.g., immobilized to the surface of) a potentiometric sensing means such as that described, for sensing glucose, in A Seki et al., Biosensors based on light-addressable potentiometric sensors for urea, penicillin, and glucose, *Anal. Chim. Acta* 373(1):9-13 (2 Nov. 1998).

In designing an acetone-specific biosensor according to the invention, various enzymatic by-products and/or factors may be employed for the production of electrochemical signals. One group includes organic cofactors, such as NAD, NADH, NADP, NADPH, FAD, FADH, FMN, FMNH, Coenzyme A, Coenzyme Q, TTQ (Tryptophan Tryptophylquinone) and PQQ (Pyrroloquinolinequinone). For example, a PQQ-dependent dehydrogenase may oxidize isopropanol. Electrons from this reaction may be transferred through PQQ, which is reduced, and can be oxidized at the electrode or with an intervening enzyme. Other vitamins may also be used.

Enzymatic reaction by-products useful in the invention include hydrogen peroxide and ammonium.

Energetic molecules may also be used in the invention for coupling acetone metabolism to electrochemically measurable signals, including: ATP, ADP, AMP, GTP, GDP and GMP. Neither these molecules nor phosphate can be detected directly, but can be detected through coupling to a redox-by-product-producing enzyme system.

These by-products, cofactors, and energetic molecules can also be detected by non-electrochemical means as described above.

Signal Mediators

Electron transfer mediators are redox-reversible species that may be used to transfer electrons between (that is to or from) the electrically potentiated surface of an electrode and an organic species (such as a co-factor) involved in an enzymatically catalyzed reaction. Examples of electron transfer mediators include: ferrocene and derivatives, ferricyanide, hydroquinone, benzoquinone and derivatives, 2,6-dichloroindophenol, methylene blue, phenylenediamine and derivatives, phenoxazine and derivatives (for example, Meldola's blue, that is 8-dimethylamino-2,3-benzophenoxazine), and phenazine alkosulfates (for example, phenazine methosulfate, phenazine ethosulfate). In a given embodiment, one or more than one species of electron transfer mediator may be used.

Electron transfer mediators can be used to improve the kinetics of electron transfer in a given enzyme-coupled electrode system, since organic cofactors may easily impair detector functions. This impairment is caused by the creation of free radicals via singly transferring multiple electrons between organic species and the electrically potentiated surface of the electrode. These free radicals then can exhibit dimer and/or polymer formation at the electrically potentiated surface, which fouls the surface of the electrode, thereby inhibiting efficient electron transfer. Electron transfer mediators can be employed to avoid this fouling of electrodes. Electron transfer mediators may also be used in situations where a shift in electrode voltage is desired, for example, where the preferred voltage for use in the reaction system without such a mediator happens to be a potential at which too much electrical interference ("noise") occurs. An electron transfer mediator may be added in order to permit a shift in the applied voltage to a different voltage region in which less noise occurs. Examples of diffusional electron-transfer mediators applicable to immobilized enzymes such as glucose oxidase, horseradish peroxidase, and the like, are set forth in Table 5 of Willner and Katz.

Preferred mediators useful in multi-electron transfers for reduced forms of, for example, NADH, NADPH, FADH, FMNH, Co-Q, PQQ, include, for example: ferrocene and derivatives, ferricyanide, hydroquinone, benzoquinone and derivatives, 2,6-dichloroindophenol, methylene blue, phenylenediamine and derivatives, phenoxazine and derivatives (for example, Meldola's blue, that is 8-dimethylamino-2,3-benzophenoxazine), and phenazine alkosulfates (for example, phenazine methosulfate, phenazine ethosulfate).

A second group of mediator factors that may be employed for the production of electrochemical signals include inorganic cofactors such as Pt, Os, V, Mn, Fe, Co, Ni, Cu, Mo, and W (see Holm et al., Aspects of Metal Sites in Biology, Chem. Rev. 1996. 96, p. 2239-2314). Some useful enzymes contain a heme center, and thus iron (for example, cytochrome P450 monooxygenase). Also useful is amine oxidase, which contains Cu. In an alternative embodiment, a "photometric mediator" may be added to the enzyme system in order to react with a product or by-product of the enzymatic reaction(s) and thereby generate a derivative that can be, for example, photochemically, calorimetrically, fluorometrically, or (UV or IR) spectrometrically detected. Thus, the addition of such a "photometric mediator" may be characterized as permitting the conversion of a result of the enzymatic reaction, that is a product or by-product, into a photometric signal. For example, in the case of enzymatically catalyzed redox reactions, a chromogenic redox indicator such as, for example, a tetrazolium salt, may be used as the photometric mediator. Many such chromogenic redox indicators are known in the art. Examples of tetrazolium salts include, but are not limited to: 3-(4,5-dimethylthiazol-2-yl)-2,5-diphenyl-2H-tetrazolium bromide (MTT bromide); (3-(4,5-dimethylthiazol-2-yl)-5-(3-carboxymethoxyphenyl)-2-(4-sulfophenyl)-2H-tetrazolium, inner salt (MTS; available from Promega Corp., Madison, Wis.); and (5-cyano-2,3-ditolyl tetrazolium chloride) (CTC). Such photometric mediators can be used, for example, to convert the redox "signal" of an electron transfer mediator into a photometrically detectable signal.

The enzymes and other components of the enzyme system may be immobilized in a gel layer disposed upon the electrode surface. Any of the various gels known in the art as useful for immobilization of biologics in the presence of an electrode may be used. For example, a method such as is described in PCT/US02/16140 (filed May 21, 2002) may be used to immobilize the biologic components of an acetone-specific enzyme system in a polyurethane hydrogel disposed upon an electrode.

Enzyme Arrays and Multi-Enzyme Systems

In addition to monitoring acetone in a sample per se, acetone-specific enzyme systems may be useful in biosensors having more than one enzyme system for detecting multiple substrates in a given biological sample. For example, an electrode linked to an acetone-specific enzyme system may enable subtraction of an acetone signal from an ethanol detector. Such a set up could be configured in an array, wherein at least two different detection modes or at least two different detectors would be operative for detecting ethanol and acetone. Such an array would be useful to correct for acetone interference in ethanol breathalyzer analyses.

Fluorescence detection can also be accomplished using arrays. Fluorescence sensor arrays have been described in the literature. They have been used for such complex samples as wine aromas, perfume, and genes. Fluorescence sensor arrays employ fluorescent or chromogenic dyes or substrates that covalently attached to polystyrene beads in wells on the distal face of an optical fiber (D. R. Walt, Imaging optical sensor arrays. Curr. Opin. Chem. Biol. 6:689 (2002)). A high-density optical array can contain several types of dyes or substrates for different analytes. The array is exposed to each possible component individually, then to the sample. Pattern recognition is employed to deduce the composition of the sample. In the case of breath or bodily fluid components, the acetone-specific enzymes, cofactors, and chromogenic or fluorogenic dyes can be covalently attached to a portion of beads, while enzymes specific for other analytes, such as ethanol, can be attached to other beads. Each bead will "light up" upon exposure to its target analyte.

An enzyme-based fluorescence or chromogenic array has never been applied to the detection of acetone.

Uses for an Acetone-Specific Enzymatic Biosensor

Breath acetone monitoring is a useful tool for monitoring effectiveness and compliance of subjects on weight loss diets. Ketosis can be manipulated by exercise and dieting choices, even between two diets with equal energy balance.

The response time for reflecting diet and exercise choices in breath acetone levels is in the order of 2-3 hours, and was a better indicator of fat loss than urine ketone analysis.

A home acetone diagnostic biosensor would be useful in aiding subject management of Type 1 and Type 2 diabetes. Such biosensors would enable subjects to monitor weight loss, to detect signs of the onset of ketoacidosis, and to control sugar intake with respect to insulin availability, especially in Type 1 diabetics. Indicators suggest that weight loss success would be improved if subjects could share daily acetone measurements with health care professionals and peers via the Internet and weekly support group meetings. Use of the inventive acetone-specific detection system is not limited to management of obesity and diabetes. It is contemplated that the acetone-specific biosensors described herein would be useful for managing any disease in which acetone production is an indicator of pathology.

In addition, the acetone-specific enzyme system may prove to be a highly effective means of monitoring subject compliance with prescribed therapeutic regimes via drug tagging with acetoacetate or a derivative thereof. The degradation of acetoacetate to acetone could be measured via a biosensor containing the inventive acetone-specific enzyme system, thereby improving the ability of health care professionals to track the dosing and bioavailability of the corresponding tagged drug.

EXAMPLES

Acetone-specific enzyme systems and acetone sensors utilizing these systems have been developed. Enzyme identification and/or purification, enzyme characterization and selection, enzyme-plus-cofactor systems, multiple-enzyme-plus cofactor systems, coupled enzyme systems providing linear (stoichiometric) acetone detection, coupled enzyme systems providing amplified (for example, exponential) acetone detection, enzyme and enzyme system stability testing, acetone vapor-to-liquid partitioning studies, and enzyme-mediated acetone sensor devices (both electrochemical and non-electrochemical devices) that utilize such systems sensors are disclosed below in particular exemplified embodiments. These examples are provided for exemplification and are not intended to limit the invention. Particular embodiments employing acetone-specific enzyme systems in enzyme-based electrochemical and non-electrochemical sensors is described below.

Materials & Methods

Materials. Acetone carboxylase from *X. autotrophicus* strain Py2 and isopropanol-grown *X. autotrophicus* strain Py2 cell paste were obtained from Professor Scott A. Ensign at Utah State University, Logan, Utah. Acetone carboxylase from *Rhodobacter capsulatus* B10 (ATCC 33303), acetone-grown *R. capsulatus* B10 cell paste, propane-grown *Mycobacterium vaccae* JOB5 (ATCC 29678) cell-free extracts, and propane-grown *Rhodococcus rhodochrous* B276 (ATCC 31338) cell paste were also obtained from Professor Ensign, and all of these bacterial strains are publicly available. Secondary alcohol dehydrogenase from *X. autotrophicus* strain Py2 and isopropanol-grown *X. autotrophicus* strain Py2 were isolated from cell paste; and exemplary, publicly available secondary alcohol dehydrogenases are described in Table 1. Pyruvate kinase (EC 2.7.1.40), myokinase (EC 2.7.4.3), pyruvate oxidase (EC 1.2.3.3), horseradish peroxidase (EC 1.11.1.7), lactate dehydrogenase (EC 1.1.1.28), malic enzyme (EC 1.1.1.40), alcohol dehydrogenase (EC 1.1.1.2), alanine dehydrogenase (EC 1.4.1.1), alcohol dehydrogenase (EC 1.1.1), alcohol oxidase (EC 1.1.3.13), and β-hydroxybutyrate dehydrogenase (EC 1.1.1.30) were purchased from Sigma (St. Louis, Mo.). All other chemicals and reagents used were analytical grade. All solutions were prepared in 18 M water (Millipore).

TABLE 1

Information for Some Publicly Available S-ADH Enzymes

| Cofactor | Organism | Source | Reference(s) [& Comments] |
|---|---|---|---|
| NADPH | *Thermoanaerobium brockii* | Sigma Chem. Co. (catalog no. A8435) | RJ Lamed et al., Enzyme & Microb. Technol., 3:144 (1981); RJ Lamed & JG Zeikus, Biochem. J, 195(1):183-90 (Apr. 1, 1981); A Ben-Bassat et al., J Bact., 146(1): 192-99 (April 1981); [DNA sequence available in GenBank (Acc. No. X64841)] |
| NADH | *Mycobacterium vaccae* strain JOB5 (Gram-positive) | ATCC 29678 | JP Coleman et al., J Gen. Microbiol., 131(11):2901-07 (November 1985); [Describes enzyme purification] |
| NADH | *Pseudomonas* sp. 6307 [CRL 75] (Gram-negative) | ATCC 21439 | CT Hou et al., Eur. J Biochem., 119(2):359-64 (October 1981); [Describes enzyme purification] |
| NADH | *Xanthobacter autotrophicus* strain Py2 | ATCC PTA-4779 | [Enzyme purification and characterization described herein] |
| NADPH | *Thermoanaerobacter ethanolicus* 39E | ATCC 33223 | DS Burdette et al., Biochem. J 316(1):115-22 (May 1996); [Describes enzyme purification, gene cloning & DNA sequencing] |
| NADH | *Candida utilis* (yeast) | DSM 70167; ATCC 26387 | H Schutte et al., Biochim. et Biophys. Acta, 716(3):298-307 (Jun. 16, 1982); [Describes screening for S-ADH activity in several yeast strains] |

TABLE 1-continued

Information for Some Publicly Available S-ADH Enzymes

| Cofactor | Organism | Source | Reference(s) [& Comments] |
|---|---|---|---|
| NADPH | "Anaerobic extremely thermophilic bacterium" | Biocatalysts Ltd. (Wales; catalog no. S300) | — |
| NADH | *Candida boidinni* (yeast) | Fluka (Milwaukee, WI; catalog no. 91031) | — |
| NADH | *Candida* sp. (yeast) | NovaBiotec Dr. Fechter GmbH (Berlin, Germany; catalog no. "Isopropanol dehydrogenase (E.C. 1.1.1.80)") | — |

Enrichment and isolation of acetone-, isopropanol-, and propane-utilizing microorganisms. Enrichment cultures were set up in 160 mL serum bottles that were crimp-sealed with butyl rubber stoppers. The bottles contained 10 mL mineral salts medium containing (in g/L): $NaNH_4HPO_4$ (1.74); $NaH_2PO_4 \times H_2O$ (0.54); KCl (0.04); $MgSO_4 \times 7\ H_2O$ (0.2) and 1 mL/L of a trace element stock solution (stock solution (in g/L): $FeCl_2 \times 4\ H_2O$ (5.4); $MnCl_2 \times 4\ H_2O$ (1.0); $ZnSO_4 \times 7\ H_2O$ (1.45); $CuSO_4 \times 5\ H_2O$ (0.25); concentrated HCl (13 mL/L); $(NH_4)_6Mo_7O_{24} \times 4\ H_2O$ (0.1); $H_3BO_3$ (0.1); $CoCl_2 \times 6\ H_2O$ (0.19)). The pH of the medium was adjusted to pH 7.2. Enrichments for propane-utilizing microorganisms were inoculated with about 0.5 g of soil that had been purchased from a local supplier of top soils, or with about 0.5 g of non-sterilized potting soil or organic compost that had been purchased from a local supermarket.

Gaseous propane was added with a syringe to a 20% (v/v) concentration in the headspace of the serum bottle. Enrichments for acetone- and isopropanol-utilizing microorganisms were set up in a similar way except that substrates were added from a 1 M stock solution to a final concentration of 25 mM acetone, or 10 mM isopropanol. The enrichment cultures were incubated on a shaker at 28° C. For the isolation of single colonies, enrichment cultures were cultivated on mineral salts medium (as described above) containing 1.5% w/v agar (hereinafter "mineral salts agar").

In a different set-up, enrichment cultures were started for acetone-utilizing microorganisms that could grow in the presence of a $CO_2$-trap. 20 mL of mineral salts medium with trace elements (see above) was filled into 250 mL baffled Erlenmeyer flasks. The medium was inoculated with about 0.5 g of soil sample (see above). The Erlenmeyer flask was closed with a rubber stopper that had been modified to hold a glass bulb. The glass bulb contained about 0.5 mL of 50% (w/v) KOH. The KOH trapped the $CO_2$ from the Erlenmeyer flask headspace. These set-ups were designed to enrich for acetone-utilizing microorganisms with an acetone carboxylase-independent pathway. The enrichment cultures were incubated on a shaker at 28° C.

Enrichment cultures were transferred two to three times after turbidity indicated bacterial growth (usually after 3 to 5 days). To isolate single colonies, enrichment cultures were spread on mineral salts agar plates. For the isolation of propane-utilizers, the agar plates were placed in a 3.5 L anaerobic jar. Propane was added to the jar until a positive pressure of 0.3-0.5 bar was reached inside the jar. The jar was placed into an incubator at 28° C. For the isolation of acetone-utilizing microorganisms, the agar plates were placed into a 1.4 L desiccator. The desiccator contained two open glass vials with 3-4 mL neat acetone each. The desiccator was sealed with several layers of PARAFILM (a wax-based sealing film, from American National Can, Chicago, Ill.) before it was placed in an incubator at 28° C. For the isolation of acetone-utilizing microorganisms that would grow in the presence of a $CO_2$-trap, agar plates were placed in a desiccator as described above. In addition to a vial with acetone, a vial containing 50% KOH (about 4 mL) was placed into the desiccator. Alternatively, for the isolation of acetone- and isopropanol-utilizers, enrichment cultures were transferred to agar plates containing mineral salts medium plus acetone or isopropanol. Additional acetone or isopropanol was added onto a small foam plug that was placed inside the Petri dish. The Petri dish was sealed with several layers of parafilm to reduce evaporation of substrates during incubation.

Colonies were visible on the agar plates after 5-10 days. Isolates were transferred to fresh agar plates and incubated as described above. Isolated strains were also streaked onto nutrient agar to check for purity. After several transfers on agar plates, 31 strains were isolated that looked different as evaluated by colony morphology. Eight strains were isolated from propane enrichments (these were designated TDCC Prop 1-8), eight strains were isolated from isopropanol enrichments (these were designated TDCC IP-1-8) and fifteen strains were isolated from acetone enrichments (these were designated TDCC Ac 1-15). None of these were obtained from an acetone+KOH-trap enrichment.

Screening of isolates and culture collection strains for growth on acetone, propane, or isopropanol. Isolates and culture collection strains were screened for growth on acetone, propane, and isopropanol in 60 mL-serum vials containing 5 mL of medium plus 0.005% (w/v) yeast extract as described above. The medium was inoculated from a single colony. Isopropanol was added from a stock solution to a final concentration of 8 mM. Cultures that showed more turbidity with substrates compared to cultures without substrates (medium blanks) were considered hits. Hits were then screened for growth with acetone in the presence of a $CO_2$-trap as described above.

Cultivation of isolates/strains, harvesting, and preparation of cell-free extracts. Several isopropanol-utilizing strains were cultivated in larger batches for initial purification of secondary alcohol dehydrogenase and experiments with cell-free extracts. Strain *Rhodococcus rhodochrous* B276

(ATCC 31338) (formerly *Nocardia corallina* B276) and strain TDCC IP-1 (and two additional strains: data not shown) were cultivated in 2×500 mL batches of mineral salts medium (for composition see above) plus 0.005% yeast extract. Isopropanol (8 mM) was added initially as carbon and energy sources. Cultures were incubated on a shaker (200 rpm) at 30° C. Growth was followed by monitoring the optical density at 600 nm. More isopropanol was added at several time points when the growth rate decreased due to lack of substrate. A total of about 96 mM isopropanol was added to the cultures. At the end of the logarithmic growth phase, cells were precipitated by centrifugation (GSA rotor, 8,500 rpm, 20 min.) at 4° C. The cells were washed once in 50 mM Tris-HCl buffer, pH 7.5. The cell pellet was weighed and resuspended in a small volume of TRIS (2-amino-2-hydroxymethyl-1,3-propanediol) buffer (about 2 mL per g cells (wet weight)). Cells were frozen at −20° C. until further use. For the preparation of cell-free extracts, cells were thawed and broken by sonication (4×20 s, pulsed, 50% intensity). Cell debris and unbroken cells were precipitated by centrifugation for 5 min. at 14,000 rpm (in an Eppendorf benchtop centrifuge, Model 5417C, Brinkmann, Instruments, Inc., Westbury, N.Y.). Alternatively, for larger preparations, the cell suspension was passed three times through a mini-French pressure cell at 20,000 psi (137,895.2 kPa), and the lysate was clarified by centrifugation at 6,000×g for 40 min at 4° C.

Protein purifications. Acetone carboxylase from *X. autotrophicus* strain Py2 and acetone carboxylase from *R. capsulatus* were purified as described previously. Secondary alcohol dehydrogenase (S-ADH) from *X. autotrophicus* Py2 was purified via the following protocol. Cell-free extracts (380 mL) of isopropanol-grown *X. autotrophicus* Py2 (150 g) were prepared as described above, and applied to a 5×15 cm column of DEAE-Sepharose FAST FLOW (Diethylaminoethyl cross-linked agarose bead material; Catalog number 17-0709-10, Amersham Pharmacia Biotech, Piscataway, N.J.)) equilibrated in buffer A (25 mM MOPS (3-(N-morpholino)propanesulfonic acid), pH 7.6, 5% glycerol, 1 mM dithiothreitol) at a flow rate of 10 mL/min. After loading, the column was washed with 1000 mL buffer A and developed with a 2400 mL linear gradient of 90-290 mM KCl in buffer A. Fractions containing S-ADH activity were pooled and dialyzed against 2 L of 25 mM potassium phosphate (pH 6.2) containing 5% glycerol (buffer B) for 16 h at 4° C. The protein was then applied to a RED SEPHAROSE CL-6B (Procion Red HE-3B dye-linked, cross-linked-agarose bead material, affinity matrix for affinity chromatograph; Catalog number 17-0528-01, Amersham Pharmacia Biotech) column (1.5×10 cm) equilibrated in buffer B at a flow rate of 2 mL/min. After washing the column with 30 mL of buffer B, S-ADH was eluted with 20 mL of buffer A containing 10 mM NAD$^+$. Fractions containing S-ADH were then dialyzed against 2 L of buffer A for 16 h at 4° C., concentrated by ultrafiltration (using a YM30 ultrafiltration membrane; catalog no. 13722, from Millipore, Bedford, Mass.), and frozen in liquid nitrogen. Partially purified S-ADH from bacterial screen cultures was prepared as follows: cell-free extracts from 1 to 5 g of cell paste were prepared as described above and applied to a 5 mL HI TRAP Q column (quaternary, tetraethylammonium, cross-linked agarose bead material for use as an anion exchange matrix; catalog number 17-1153-01, Amersham Pharmacia Biotech) equilibrated in 100 mM MOPS, pH 7.6, containing 5% (v/v) glycerol (buffer C). The column was washed with 10 mL buffer C and developed with a 100 mL linear gradient of 0 to 100 mM NaCl in buffer C. Fractions containing S-ADH activity were pooled, concentrated to 0.5 mL using a 30 kDa MWCO ("molecular weight cut-off") centrifugal membrane (catalog number UFV4BTK25, Millipore), and stored at −80° C.

Example 1

Acetone carboxylase coupled to NADH oxidation spectrophotometric assay. Assays were performed in 2 mL (1 cm path length) quartz cuvettes that had been modified by fusing a serum bottle-style quartz top (7×13 mm at mouth), allowing the cuvettes to be sealed with a red rubber serum stopper. The reaction mix contained ATP (10 mM), MgCl$_2$ (11 mM), potassium acetate (80 mM), MOPS (100 mM), CO$_2$ (50 mM (1 mol CO$_2$(g) to 4 mol potassium bicarbonate to maintain pH)), and 20 to 40 μg purified acetone carboxylase in a total volume of 1 mL at pH 7.6. The addition of β-hydroxybutyrate dehydrogenase (3 U) and NADH (0.2 mM) allowed acetoacetate formation to be coupled to the oxidation of NADH. Assays were pre-incubated for 2 min. at 30° C. with all assay components except acetone. Assays were initiated by addition of acetone (2 mM). The reaction was monitored by measuring the decrease in absorbance at 340 nm ($\epsilon_{340}$ of 6.22 mM$^{-1}$·cm$^{-1}$ for NADH) over time in an Agilent Technologies (Palo Alto, Calif.) model 8453 UV-Visible Spectroscopy System containing a thermostat-controlled cell holder at 30° C.

Acetone carboxylase coupled to H$_2$O$_2$ formation spectrophotometric assay. Assays were performed in 2 mL (1 cm path length) quartz cuvettes and contained ATP (0.1 mM), MgSO$_4$ (10 mM), potassium acetate (80 mM), potassium phosphate (50 mM), CO$_2$ (50 mM (1 mol CO$_2$(g) to 4 mol potassium bicarbonate to maintain pH)), 40 μg purified acetone carboxylase, phosphoenolpyruvate (2 mM), pyruvate kinase (20 U), myokinase (15 U), pyruvate oxidase (2 U), peroxidase (15 U), flavin adenine dinucleotide (0.01 mM), cocarboxylase (0.2 mM), 4-aminoantipyrine (0.5 mM), and N-ethyl-N-(2-hydroxy-3-sulfopropyl)-m-toluidine (0.02% w/v) in a total volume of 1 mL at pH 7.5. Coupling enzymes and reagents (that is phosphoenolpyruvate, pyruvate kinase, myokinase, pyruvate oxidase, flavin adenine dinucleotide, and cocarboxylase,) allowed ATP hydrolysis to be coupled to H$_2$O$_2$ formation (pyruvate oxidation). Addition of peroxidase, 4-aminoantipyrine, and N-ethyl-N-(2-hydroxy-3-sulfopropyl)-m-toluidine allowed H$_2$O$_2$ formation to be monitored spectrophotometrically at 550 nm ($\epsilon_{550}$ of 36.88 mM$^{-1}$·cm$^{-1}$ for quinoneimine dye product) over time in a thermostat-controlled cell holder at 30° C. Assays were pre-incubated for 2 min. at 30° C. with all assay components except acetone. Assays were initiated by addition of acetone (5 mM).

Example 2

Secondary alcohol dehydrogenase NADH oxidation spectrophotometric assay. Assays were performed in 2 mL quartz cuvettes and contained NAD(H) (0.2 mM), potassium phosphate buffer (25 mM), and a source of enzyme (cell-free extracts, column fractions, or purified enzyme) in a total reaction volume of 1 mL at pH 6.2 (for ketone reduction assays) or pH 7.8 (for alcohol oxidation assays) at 30° C. Assays were pre-incubated for 1.5 min. at 30° C. with all assay components except substrate. Assays were initiated by addition of substrate (2.5 mM) and monitored over time by measuring the change in absorbance at 340 nm ($\epsilon_{340}$ of 6.22 mM$^{-1}$·cm$^{-1}$ for NADH).

Secondary alcohol dehydrogenase coupled to H$_2$O$_2$ formation spectrophotometric assay. Assays were performed in 2 mL (1 cm path length) quartz cuvettes and contained potassium phosphate (50 mM), 1.5 µg purified S-ADH, NADH (50 µM), lactate (10 mM), lactate dehydrogenase (20 U), pyruvate oxidase (2 U), peroxidase (15 U), flavin adenine dinucleotide (0.01 mM), cocarboxylase (0.2 mM), 4-aminoantipyrine (0.5 mM), and N-ethyl-N-(2-hydroxy-3-sulfopropyl)-m-toluidine (0.02% w/v) in a total volume of 1 mL at pH 6.2. Coupling enzymes and reagents (that is lactate, lactate dehydrogenase, pyruvate oxidase, flavin adenine dinucleotide, and cocarboxylase) allowed NADH oxidation to be coupled to $H_2O_2$ formation (pyruvate oxidation). In some assays (where specified), lactate and lactate dehydrogenase were replaced with alanine (10 mM) and alanine dehydrogenase (2 U). Assays were monitored spectrophotometrically at 550 nm ($\epsilon_{550}$ of 36.88 $mM^{-1} \cdot cm^{-1}$ for quinoneimine dye product) over time in a thermostat-controlled cell holder at 30° C. as described above. Assays were pre-incubated for 2 min. at 30° C. with all assay components except acetone. Assays were initiated by addition of acetone (2.5 mM).

Primary alcohol dehydrogenase coupled to primary alcohol oxidase substrate recycling assays. Assays were performed in 2 ml (1 cm path length) quartz cuvettes and contained potassium phosphate (25 mM), alcohol dehydrogenase (1 U), NADH (100 µM), alcohol oxidase (2 U), peroxidase (15 U), 4-aminoantipyrine (0.5 mM), and N-ethyl-N-(2-hydroxy-3-sulfopropyl)-m-toluidine (0.02% w/v) in a total volume of 1 mL at pH 6.2. Assays were monitored spectrophotometrically at 550 nm ($\epsilon_{550}$ of 36.88 $mM^{-1} \cdot cm^{-1}$ for quinoneimine dye product) or at 340 nm ($\epsilon_{340}$ of 6.22 $mM^{-1} \cdot cm^{-1}$ for NADH) over time in a thermostat-controlled cell holder at 30° C. as described above. Assays were pre-incubated for 2 min. at 30° C. with all assay components except ethanol. Assays were initiated by addition of ethanol (50 µM or 5 µM).

Stability studies. A sufficient quantity of enzyme for each individual activity assay (for example, 1.5 µg S-ADH) was aliquoted into 1.5 mL microcentrifuge tubes with specified concentrations of additives (for example trehalose (10% w/v)) in buffer (25 mM MOPS, pH 7.6) and frozen at −80° C. for 1 h. Samples were then placed in a shelf freeze dryer (Virtis model Advantage ES) and held at −50° C. (shelf temperature) for 16 h, and then increased to 20° C. for 4 h. Freeze-dried samples were removed and allowed to sit at room temperature (17 to 24° C.) over time. At specified time points, samples were re-hydrated and assayed as described above.

Protein characterizations. Sodium dodecyl sulfate-polyacrylamide gel electrophoresis (SDS-PAGE) was performed following the Laemmli procedure (Laemmli, U.K., Nature, 227:680-685 (1970)) using a 12% T, 2.7% C gel. "% T" indicates weight percent of total monomers, a measure of total monomer concentration, which is given by % T=100× ((grams acrylamide)+(grams cross-linker))/total gel volume (in mL); "% C" indicates weight percent of cross-linker, which is given by % C=100×(grams cross-linker)/((grams acrylamide)+(grams cross-linker)); and the cross-linker used was N,N'-methylene-bis-acrylamide. Electrophoresed proteins were visualized by staining with Coomassie Blue (PhastGel Blue R, catalog number 17-0518-01, Amersham Pharmacia Biotech). The apparent molecular masses of polypeptides based on SDS-PAGE migration were determined by comparison with $R_f$ values of standard proteins. N-terminal sequencing was performed by Commonwealth Biotechnologies, Inc. (Richmond, Va.). Protein concentrations were determined by using a modified biuret assay (V. J. Chromy et al., Clin. Chem, 20:1362-63 (1974) with δ-globulin as the standard.

Mass spectrometry analysis of enriched S-ADH and generation of peptide amino acid sequences was performed as follows. The S-ADH soluble protein was characterized by high-resolution two-dimensional gel electrophoresis. Proteins (30 µg) were solubilized for isoelectric focusing (IEF) analysis in rehydration sample buffer consisting of 5 M urea, 2 M thiourea, 2% (w/v) CHAPS (3-[(3-cholamidopropyl) dimethylammonio]-1-propanesulfonate), 2% (w/v) SB 3-10 (2-(decyldimethylammonio)propanesulfonate), 40 mM TRIS, 2 mM tributyl phosphine (added to rehydration solution just before use), and 0.2% Bio-Lyte 3/10 (Bio-Rad, Hercules, Calif., cat. no. 163-2104). Protein/rehydration solution was rehydrated into 11 cm IPG ReadyStrip pH 3-10 (Bio-Rad, Cat. no. 163-2014) under passive conditions 0 volts, 20° C., 16 hrs.

One-dimensional isoelectric focusing was carried out on a Protean IEF cell (Bio-Rad, model no. 526BR02142) for 35,000 volt-hours using IPG ReadyStrips (Bio-Rad). Following first dimension electrophoresis, gels were equilibrated for 20 minutes in a buffer containing 20% glycerol, 0.375 M Tris, 6 M urea, 2% SDS, and 5 M tributyl phosphine. IPG ReadyStrips were placed on top of a Criterion™ precast 1 mm 4-20% gradient Tris-HCl-SDS gel (Bio-Rad, cat. no. 345-0036) and 0.5% warm Agarose containing 0.01% bromophenol blue (Bio-Rad, cat. no. 161-0404) was added to the remaining well. Electrophoresis was carried out on a Criterion mini electrophoresis cell (Bio-Rad, cat. no. 165-6001) at room temperature. The electrophoresis running buffer was prepared from a 10× Tris-glycine-SDS solution (Bio-Rad, cat. no. 161-0732). Following assembly of the gel system and addition of the running buffer, the electrophoresis was carried out at an initial current of 2 mA, 3500 volts, 45 watts, for 1.5 hrs. The current was ramped up to 5 mA for 30 minutes followed by 10 mA for 2-3 hrs. Typical run times were between 4-5 hrs. Following electrophoresis, gels were stained in a buffer consisting of 17% ammonium sulfate, 30% methanol, 3% phosphoric acid, and 0.1% coomassie brilliant blue G250 (Bio-Rad, cat no. 161-0436), for at least 12 hrs. Gels were rinsed with water and stored in 2% acetic acid until further processing.

Colloidal Coomassie-stained gel images were captured using Bio-Rads Fluor-S MultiImager (Bio-Rad, cat. no. 170-7700). Digital filtering algorithms were used to remove non-uniform background without removing critical image data. Internal standards (molecular weight markers) were used initially to determine the molecular weight of the targeted proteins of interest. The molecular weight and pI of the S-ADH protein were determined by comparison of its position on the two-dimensional gel relative to the protein standards.

Protein spots relative to S-ADH from the 2-D gel were excised manually. The gel pieces were macerated and destained with 25 mM ammonium bicarbonate/50% acetonitrile in a 1.5 mL microfuge tube with vigorous shaking for 30 minutes. The blue-tinted destaining solution was removed and discarded with a fine-tip pipette. The destaining step was repeated until the stain was removed from the gel pieces. The gel pieces were dried under vacuum for 10 to 15 minutes. Proteins were digested overnight at 37° C. in a total volume of 25 µL of sequence-grade, modified trypsin (Roche Diagnostics, Indianapolis, Ind.) at a final protein of 25 ng/µL in 25 mM ammonium bicarbonate. Peptides were eluted with 50% acetonitrile and 0.5% trifluoroacetic acid.

All peptide samples were concentrated, desalted, and detergents removed by using C18 reversed-phase ZipTip™ pipette tips as described by the manufacturer (Millipore, Bedford, Mass., cat. no. ZTC18SO96).

The resulting tryptic peptides were analyzed directly by mass spectrometry. Mass spectrometry experiments were carried out on a PerSeptive Biosystems (Framingham, Mass.) Voyager DE-STR equipped with a $N_2$ laser (337 nm, 3-nsec pulse width, 20-Hz repetition rate). The mass spectra were acquired in the reflectron mode with delayed extraction. Internal mass calibration was performed with low-mass peptide standards, and mass-measurement accuracy was typically ±0.1 Da. All peptide samples were diluted in α-cyano-4-hydroxycinnamic acid, which had been prepared by dissolving 10 mg in 1 mL of aqueous 50% acetonitrile containing 0.1% trifluoroacetic acid.

Several tryptic peptide masses from S-ADH were further sequenced by one of the following approaches by mass spectrometry as described below.

Approach 1: Tryptic digests of the protein were derivatized with chlorosulfonylacetyl chloride reagents as described by Keough T., Lacey M. P., Youngquist R. S. *Proc. Natl. Acad. Sci. USA* 1999; 96 7131. The sulfonated sample was acidified with trifluoroacetic acid and cleaned up directly using C18 mini-columns (ZipTips™, Millipore). The derivatized peptides were eluted into α-cyano-4-hydroxycinnamic acid (Fluka, cat. no. 28480) and plated directly onto MALDI plates. Derivatized peptides were analyzed on an Applied Biosystems Voyager DE-STR time-of-flight mass spectrometer equipped with a $N_2$ laser. All mass spectra were acquired in the reflectron mode with delayed extraction. External mass calibration was performed with low-mass peptide standards, and mass measurement accuracy was typically ±0.2 Da. PSD fragment ion spectra were obtained after isolation of the appropriate derivatized precursor ions using timed ion selection. Fragment ions were refocused onto the final detector by stepping the voltage applied to the reflectron in the following ratios: 1.0000 (precursor ion segment), 0.9000, 0.7500, 0.5625, 0.4218, 0.3164, and 0.2373 (fragment ion segments). The individual segments were stitched together using software developed by Applied Biosystems. All precursor ion segments were acquired at low laser power (variable attenuator=1980) for 100 laser pulses to avoid detector saturation. The laser power was increased (variable attenuator=2365) for the remaining segments of the PSD acquisitions. The PSD data were acquired at a digitization rate of 20 MHz; therefore, all fragment ions were measured as chemically averaged and not monoisotopic masses.

Approach 2: Sequence tags were obtained from S-ADH tryptic peptides. Post source decay (PSD) fragment ion spectra were acquired for four peptides after isolation of the appropriate precursor ion by using timed ion selection. Fragment ions were refocused onto the final detector by stepping the voltage applied to the reflector in the following ratios: 1.0000 (precursor ion segment), 0.9000, 0.7500, 0.5625, 0.4218, 0.3164, and 0.2373 (fragment segments). The individual segments were stitched together by using software provided by PerSeptive Biosystems. All precursor ion segments were acquired at low laser power (variable attenuator=1,450) for <256 laser pulses to avoid saturating the detector. The laser power was increased for all of the remaining segments of the PSD acquisitions. Typically, 200 laser pulses were acquired for each fragment-ion segment. The PSD data were acquired at a digitization rate of 20 MHz. Mass calibration was performed with peptide standards. Metastable decompositions were measured in all PSD mass spectrometry experiments.

Approach 3: Sequence tags were obtained from S-ADH tryptic peptides by ESI MS/MS the mass spectra were acquired on a Micromass Q-TOF2 quadrupole/time of flight MS system.

Example 3

Initial electrochemical measurement of NADH and correlation to spectrophotometric data. 10 micron disc carbon fiber microelectrodes were purchased (from Bioanalytical Systems ("BAS"), West Lafayette, Indiana (part number MF-2007)) and pretreated using the method of Kuhr et. al. (63). The electrode surface was polished for 10 min. with 1 μm diamond paste (Bioanalytical Systems) and sonicated in hot toluene for 2 min. To remove residual polishing material, the microelectrode was rinsed once in methanol and once in water, then sonicated twice in water for 1 min. The polished microelectrode was subsequently pretreated electrochemically in 1 M HCl by twice applying 10 cycles of 100 V/s from −200 mV to +1800 mV. Then the microelectrode was treated in 100 mM potassium phosphate buffer by twice applying 10 cycles of 0 to +1200 mV at 100 mV/s. Background scans were then obtained from phosphate buffer alone. All potentials were referenced versus a Ag/AgCl reference electrode (Bioanalytical Systems). After baseline fast-scan cyclic voltammograms (CVs) were obtained for the enzyme (1 U/mL) and NAD(P)H (2 mM), the required volume of aqueous acetone was added (20 mM final concentration). The solution was quickly mixed, and fast-scan CVs were obtained every 1 min. for 25 min. The buffer-only background was subtracted from each CV with BAS 100W electrochemical software version 2.3 (obtained from Bioanalytical Systems, West Lafayette, Ind., hereinafter "BAS").

Unless otherwise indicated, all electrochemical measurements were performed using a Bioanalytical Systems (BAS) Model 100A or B electrochemical analyzer coupled to a BAS PA-1 preamplifier and a Faraday cage (part number MF-2500), wherein all waveforms were generated and currents acquired via BAS 100W electrochemical software version 2.3. The data were processed using Microsoft Excel 97 SR-2 and BOMEM GRAMS/32 version 4.04, Level II (Galactic Industries Corporation). The electrochemical cell was a custom-built 0.20 mL cell, constructed from Plexiglas (acrylic polymer sheet, from Atofina Corp., Paris, France), containing a Ag/AgCl reference electrode, the pretreated carbon fiber microelectrode, and a Pt wire auxiliary electrode.

To correlate spectrophotometric with electrochemical data for both enzymes, the same reaction conditions were used for both analyses. For S-ADH from *T. brockii*, the 1 mL reaction volume comprised final concentrations of 2 mM NADPH, 20 mM acetone, and 1 U S-ADH. For S-ADH from *X. autotrophicus* Py2, the 1 mL reaction volume comprised final concentrations of 2 mM NADH, 20 mM acetone, and 1 U S-ADH. For both reactions, baseline $A_{340}$ was obtained for the enzyme and NAD(P)H versus a phosphate buffer blank. The cuvette containing the reaction solution was then removed from the spectrophotometer, and the 0.4 mL of solution was removed from the cuvette and combined with the remaining 0.6 mL. The required volume of aqueous acetone was added to the 1.0 mL reaction. The solution was mixed, 0.4 mL was added to the cuvette, and the cuvette replaced in the spectrophotometer. The decrease in $A_{340}$ was then monitored for 30 min. using a Shimadzu UV-VIS-NIR scanning spectrophotometer (model UV-3101PC, Colombia, Md.). Data were acquired using UVPC Personal Spectroscopy Software version 3.9 (Shimadzu, Colombia, Md.) and processed using Microsoft Excel 97 SR-2. Quartz cuvettes with a 1 mm pathlength and a 0.4 mL volume were purchased (from Fisher Scientific, Pittsburgh, Pa., part number 14-385-906A).

Electrochemical measurement of acetone-dependent NADH consumption using Meldola's Blue-modified carbon electrodes. A glassy carbon disk electrode modified with the electrocatalyst Meldola's blue was prepared as follows. A 3-mm diameter glassy carbon electrode (BAS part number MF-2012) was first wet-polished with a 1 m diamond suspension, sonicated in deionized water for one minute, and then further polished with 0.05 m alumina polishing suspension. The freshly polished electrode was washed thoroughly by sonication in deionized water and subsequently pretreated electrochemically in 5 mL deoxygenated 100 mM phosphate buffer (pH 7.2) by applying 20 cycles of 5 V/s from −500 mV to +300 mV, four times. After the cycling, a constant polarizing potential at −0.5 V was applied for 60 s. The electrochemically pretreated electrode was then soaked in 0.5% of Meldola's blue (Aldrich, Milwaukee, Wis., catalog number 32,432-9) at room temperature for 30 min. The electrode was rinsed with deionized water before use.

Screen-printed carbon electrodes formulated with Meldola's Blue mediator were purchased from Gwent Electronic Materials Ltd. (Pontypool, United Kingdom). The disposable strips were configured in the geometry described by Hart et al. and consisted of two screen-printed electrodes deposited onto a polyethylene substrate. The working electrode was graphite carbon containing the electrocatalyst Meldola's Blue (part number C70902D2 from Gwent), and the reference/counter electrode was Ag/AgCl printed ink (part number C61003D7 from Gwent). The working electrode area was defined by printing an additional dielectric coating (part number D2000222D2 from Gwent). The electrode geometric area is 3×3 mm, or 9 mm$^2$. The electrodes were pre-soaked in phosphate buffer for 10 minutes before use to remove loosely bound Meldola's Blue.

The acetone-dependent consumption of NADH catalyzed by S-ADH was measured with Meldola's blue-carbon electrodes prepared as above using chronoamperometry in a 1 mL reaction volume containing 100 mM potassium phosphate buffer (pH 7.2), NADH (500 μM), S-ADH (1 U), and varying concentrations of acetone. After a 2 min. incubation period, the potential was stepped from open circuit to 68 mV (vs. Ag/AgCl) and the current was recorded after 120 s.

Measurement of acetone-dependent consumption of NADH using commercial blood glucose disposable test strips. Disposable glucose biosensor strips and reader (Precision Xtra Advanced Diabetes Management System) are available from MediSense (a division of Abbott Laboratories, Bedford, Mass.). 1 mL reaction volumes containing 25 mM potassium phosphate buffer (pH 6.2), NADH (2 mM), S-ADH (20 U), and acetone (0.5, 1.0, 1.5, 2.0 mM respectively) were incubated at room temperature. After 5 min., a 20-μL aliquot was removed from each reaction mix and applied to a disposable strip pre-inserted in the glucose meter. The meter reading value (mg/dL of glucose equivalent) was recorded and plotted to the amount of acetone added.

Secondary alcohol dehydrogenase coupled to $H_2O_2$ formation electrochemical assay. A disk platinum electrode (BAS part number MF-2013) was used to monitor $H_2O_2$ produced by the S-ADH coupled enzymatic reaction in response to acetone concentration. Before measurements the electrode surface was polished using $Al_2O_3$ paste for 1 min. and then rinsed with deionized water, sonicated for 1 min. and rinsed with water again. The polished Pt electrode was then pretreated electrochemically by applying 10 cycles of 100 mV/s from +200 mV to +900 mV. All potentials were referenced versus a Ag/AgCl electrode (BAS part number MF-2078). Assays contained potassium phosphate (100 mM, pH 7.2), purified S-ADH (1 U/mL), NADH (20 μM), lactate (100 mM), lactate dehydrogenase (5 U/mL), pyruvate oxidase (4 U/mL), flavin adenine dinucleotide (0.01 mM), cocarboxylase (0.2 mM), in a total volume of 0.5 mL. Assays were initiated by addition of acetone. After a 2 min. incubation period, the potential was stepped from open circuit to 350 mV. The oxidative current was recorded after 120 s and plotted against acetone concentration.

Disposable electrode materials were evaluated to monitor acetone-dependent $H_2O_2$ produced by the coupled enzyme reaction using the identical enzyme reagent system and similar electrochemical technique as described above for the disk platinum electrode. Screen-printed platinized carbon/graphite electrodes and cobalt phthalocyanine carbon electrodes were purchased (part numbers C2000511D1, and C40511D8, respectively, Gwent Electronics Materials, Ltd.) with the same electrode geometry as described earlier for the Meldola's Blue screen-printed carbon electrodes. Screen-printed platinized carbon electrodes were pre-soaked in phosphate buffer for 5 min. before use. Assays were initiated by addition of acetone and incubated for 2 min. at which time the potential was stepped from open circuit to 350 mV. The oxidative current was recorded after 120 s. Cobalt phthalocyanine-modified screen-printed carbon electrodes were pre-soaked in phosphate buffer for 5 min. before use. After each addition of acetone, the reaction was allowed to incubate for 3.5 min. Chronoamperometric measurements were made with an initial quiet time of 5 s at 150 mV, and then the potential was stepped to 650 mV for 30 s and the current recorded. One cobalt phthalocyanine-modified screen-printed electrode was used for each experiment and then discarded.

A prototype disposable platinized carbon electrode was constructed by cutting ⅛ inch (3.06 mm) diameter circular disks (using a manual hole puncher) of Toray carbon paper (porous carbon paper) or cloth, loaded with 20% (w/w) platinum nanoparticles (these platinum particles are nanonoparticles deposited on carbon; the platinum nanoparticle-loaded paper or cloth was purchased from ETEK Division of De Nora North America, Somerset, N.J., part number SLS-SPEC) and attached to a screen-printed carbon working electrode (part number C10903D14 from Gwent Electronics Materials, Ltd.) using double-sided carbon tape (also ⅛ inch (3.06 mm) diameter disk). In some experiments, 20 μM of non-ionic detergent TRITON X-100 (t-octylphenoxypoly-ethoxyethanol; catalog number T-8787, from Sigma Chemical Co.) or BRIJ 30 (tetraethylene glycol monododecyl ether; catalog no. P-1254, from Sigma) was applied to the ETEK material disk and allowed to dry before use. Before measurements, the electrode was pretreated electrochemically by applying 10 cycles of 100 mV/s from +200 mV to +900 mV twice. Assays were initiated by addition of acetone and incubated for 2 min. Chronoamperometric measurements were made with a quiet time of 2 s at 215 mV, and then the potential was stepped from 215 mV to 350 mV vs. Ag/AgCl. The oxidative current was recorded after 30 s.

Reflectance photometry measurement of acetone-dependent $H_2O_2$ formation using glucose disposable test strips and correlation to electrochemical data. Disposable glucose biosensor strips and reader were purchased (OneTouch Basic read and strips from Lifescan, Inc., Milpitas, Calif.). Successive additions of 100 µM acetone were added to a 1 mL reaction volume containing the S-ADH coupled enzyme system (as described above) and incubated at room temperature. Each acetone addition was allowed to react for 4 min. and then a 20-µL aliquot was removed from the reaction mix and applied to a disposable strip pre-inserted in the glucose meter. The meter reading value (mg/dL of glucose equivalent) was recorded and plotted against the total concentration of acetone. $H_2O_2$ concentration was also monitored chronoamperometrically using a disk platinum electrode as described above. The correlation between the electrochemical assay and the colorimetric readings were plotted.

Enzyme-based electrochemical measurement of gas phase acetone. Gas phase samples (0-10 ppm v/v) of acetone were prepared by injecting standard concentrations of acetone into a calibrated airbag (10 L bag, Calibrated Instruments, Inc, Ardsley, N.Y.) filled with 7 L of water-saturated air and 1 L of dry air, and allowed to evaporate at 37° C. (about 30 min.). The gas samples produced from this system closely simulate human breath in terms of temperature and moisture content. The gas sampling system was calibrated (that is, concentration of acetone gas phase and liquid phase samples) using gas chromatography with a Hewlett Packard 5890 gas chromatograph equipped with flame ionization detection and an on-column injector. 1 µL aqueous samples were applied to a 15 m long, coiled capillary column (Nukol, 0.53 mm diameter with 0.50-µm layer of liquid phase, catalog number 25326, available from Supelco, Inc., Bellafonte, Pa.). The oven temperature was held at 40° C. for 4 min., then increased at 25° C./min. to 200° C. The carrier gas flow rate was 5 mL/min. of helium.

Two types of sampling techniques were used to partition acetone from the gas phase into the liquid phase; a foam system, and a thin-aqueous layer system. For the foam system, a piece of polyurethane foam was cut into a cylindrical shape (19 mm long and 10 mm in diameter) so that the volume was about 1 mL. The foam was boiled in water for 20 min. and then inserted into a 3 cc disposable plastic syringe. The syringe plunger was inserted and pushed firmly to remove excess water and then removed. Before introducing gas phase acetone samples, 50 µL of water or phosphate buffer was loaded into the foam. Once the water contacted foam, the surface tension sucked water into the foam cell and the water distributed evenly onto foam surface. The syringe containing wetted foam was then connected via tubing to the gas sampling system and the gas sample passed through the foam with a flow rate 5 L/min. for 12 seconds either by running a diaphragm pump or by manually pushing the airbag. This allowed the total gas sample volume to equal 1 L. After sampling, the syringe containing foam was quickly disconnected and the plunger re-inserted. The liquid was then squeezed out into an electrochemical cell for electrochemical analysis or into a vial insert for gas chromatography analysis. For electrochemical measurements, the acetone-partitioned water sample was mixed with concentrated enzyme solution (S-ADH and coupling enzymes as discussed above) to make the desired final enzyme solutions and incubated for 2 min. The acetone-dependent $H_2O_2$ formed from the enzyme reaction was measured chronoamperometrically as described above.

For the thin aqueous layer sampling method, the gas was released from the airbag in a fine stream at a flow rate of 500 mL/min. for 2 min. so that the total volume of gas was equal to 1.0 L. In this experiment, the working electrode was inverted (electrode surface facing up), so that a small amount of enzyme solution (50 µL) forms a relatively thin layer of liquid to cover the electrode surface. The gas was blown perpendicular to the liquid surface. The gas stream stirred the liquid to enhance the mass transfer of acetone from gas phase into liquid phase. After the gas sample flow, the enzyme solution was allowed to react for 1 min. The acetone-dependent $H_2O_2$ formed from the enzyme reaction was measured chronoamperometrically as described above. The current responses were plotted against the gas-phase acetone concentration in the airbag.

The invention claimed is:

1. A hand-held medical apparatus comprising:
   a. a housing;
   b. an inlet for receiving a sample of user breath;
   c. a sensor for detecting acetone in said user breath using a biomolecule and producing a breath-component signal over a measurement time;
   d. a sensing electrical circuit in electrical communication with said sensor for sensing said breath-component signal, wherein the magnitude of said breath-component signal is a function of the concentration of said acetone in said breath sample to be received into said inlet;
   e. an analog to digital converter in electrical communication with said sensing electrical circuit for converting said breath-component signal to a digital signal;
   f. a microprocessor for processing said digital signal into at least one of a data signal and a user fat metabolism indicator; and
   g. a display in electrical communication with said microprocessor for displaying said at least one of a data signal and a user fat metabolism indicator.

2. The hand-held medical apparatus of claim 1, wherein said sensor is an electrochemical biosensor.

3. The hand-held medical apparatus of claim 2, further comprising means for removably retaining said electrochemical biosensor therewithin.

4. The hand-held medical apparatus of claim 1, wherein said sensor comprises:
   a. means for removably receiving a disposable test matrix comprising an enzyme that selectively targets acetone as a substrate to produce a colored product, wherein the amount of said colored product produced is a function of the concentration of acetone in said breath sample introduced into said inlet;
   b. a light source to illuminate said disposable test matrix; and
   c. a light detector to detect light reflected from said disposable test matrix and to create said breath-component signal.

5. The hand-held medical apparatus of claim 1, wherein said sensor comprises:
   a. means for removably receiving a disposable test matrix comprising an enzyme that selectively targets acetone as a substrate to produce a luminescent product, wherein the amount of said luminescent product produced is a function of the concentration of acetone in said breath sample introduced into said inlet; and
   b. a light detector to detect light emitted from said disposable test matrix and to create said breath-component signal.

6. The hand-held medical apparatus of claim 5, further comprising a light source to illuminate said disposable test matrix.

7. The hand-held medical apparatus of claim 5, wherein said disposable test matrix further comprises a working electrode, a counter electrode and a reference electrode.

8. The hand-held medical apparatus of claim 1, wherein said sensor is a thermosensor system.

9. The hand-held medical apparatus of claim 8, wherein said thermosensor comprises a reference thermosensor and working thermosensor.

10. The hand-held medical apparatus of any of claims 4-7, further comprising a compressible, porous material that is retained adjacent to said disposable test matrix and operable to transfer acetone to said disposable test matrix when said compressible, porous material is compressed.

11. The hand-held medical apparatus of any of claims 1-9, further comprising data storage means.

12. The hand-held medical apparatus of any of claims 1-9, further comprising a personal data assistant in electrical communication with said microprocessor.

13. The hand-held medical apparatus of claim 12, wherein said personal data assistant further comprises a clock for associating the time at which said breath-component signal is produced.

14. The hand-held medical apparatus of claim 12, wherein said personal data assistant further comprises user input means by which information may be inputted as user-input data, wherein said user-input data is stored and used to create a user fat metabolism indicator.

15. The hand-held medical apparatus of claim 12, wherein said personal data assistant further comprises at least one of the following:
  a. outgoing communication means by which data is transmittable to a computer external to said personal data assistant; and
  b. incoming communication means by which information from a computer is receivable by said personal data assistant device as computer input data.

16. The hand held medical apparatus of claim 1, wherein said inlet comprises a removable mouthpiece.

17. The hand-held medical apparatus of claim 16, wherein the removable mouthpiece is disposable.

18. The hand-held medical apparatus of any of claims 1-9 or 16, wherein said microprocessor integrates said digital signal as a function of said measurement time to generate said data signal.

19. The hand-held medical apparatus of claim 1, wherein the inlet is disposable.

20. The hand-held medical apparatus of claim 1, wherein said sensor comprises an enzyme that selectively targets acetone.

21. The hand-held medical apparatus of claim 20, wherein:
  at least a portion of said sensor is supported by a disposable strip comprising a gel or polymeric medium; and
  said enzyme is immobilized in said gel or polymeric medium.

22. The hand-held medical apparatus of claim 1, wherein at least a portion of said sensor is supported by a disposable physical support.

23. The hand-held medical apparatus of claim 22, wherein said disposable physical support is a disposable substrate, and said sensor comprises:
  a support layer, in which an enzyme that targets acetone is immobilized, positioned on said disposable substrate; and
  at least two electrodes, each having an end disposed in said support layer, wherein said two electrodes are electrically coupled to provide said breath component signal.

24. The hand-held medical apparatus of claim 23, wherein said support layer comprises a moisture-absorbing material.

25. The hand-held medical apparatus of claim 24, wherein said support layer is a gel layer.

26. The hand-held medical apparatus of claim 22, wherein:
  said housing comprises a conduit through which at least a portion of said user breath flows; and
  said disposable physical support is removable from said conduit for replacement after each use of the hand-held medical apparatus.

27. The hand-held medical apparatus of claim 22, wherein said sensor comprises at least two electrodes supported by said disposable physical support.

28. The hand-held medical apparatus of claim 27, wherein said two electrodes are screen-printed onto said disposable physical support.

29. The hand-held medical apparatus of claim 22, wherein said disposable physical support is a disposable strip.

30. The hand-held medical apparatus of claim 29, wherein said disposable strip is a plastic strip.

31. The hand-held medical apparatus of claim 1, wherein said sensor comprises means for removably receiving a disposable test matrix comprising an enzyme that selectively targets the acetone and wherein said disposable test matrix further comprises a working electrode, a counter electrode and a reference electrode.

32. A breath analysis apparatus comprising:
  a housing including a conduit through which a sample of user breath flows;
  a sensor, for detecting acetone in at least a portion of said sample and producing a breath-component signal, wherein said sensor comprises a biomolecule;
  a sensing circuit in electrical communication with said sensor for sensing said breath-component signal, wherein the magnitude of said breath-component signal is a function of the concentration of said acetone; and
  a processor for processing an output from said sensing circuit, corresponding to said breath-component signal, into a data signal.

33. The breath analysis apparatus of claim 32, wherein said biomolecule is an enzyme.

34. The breath analysis apparatus of claim 32, wherein at least a portion of said sensor is supported by a disposable physical support.

35. The breath analysis apparatus of claim 32, wherein said sensor is an electrochemical biosensor.

36. The breath analysis apparatus of claim 32, wherein said processor is a microprocessor.

37. The breath analysis apparatus of claim 32, wherein said sensor further comprises an electrode and said breath analysis apparatus further comprises a compressible, porous material that is retained adjacent to said electrode and operable to transfer said acetone to said electrode when said compressible, porous material is compressed.

38. A hand-held medical apparatus comprising:
  a. a housing;
  b. an inlet for receiving a sample of user breath;
  c. an electrochemical biosensor for detecting a component of said user breath using an enzyme that selectively targets acetone and producing a breath-component signal over a measurement time;

d. a sensing electrical circuit in electrical communication with said sensor for sensing said breath-component signal, wherein the magnitude of said breath-component signal is a function of the concentration of said component in said breath sample to be received into said inlet;

e. an analog to digital converter in electrical communication with said sensing electrical circuit for converting said breath-component signal to a digital signal;

f. a microprocessor for processing said digital signal into at least one of a data signal and a user fat metabolism indicator; and g. a display in electrical communication with said microprocessor for displaying said at least one of a data signal and a user fat metabolism indicator.

39. A breath analysis apparatus for detecting acetone in a person's breath, the a apparatus comprising:

a conduit through which a sample of a person's breath flows;

an electrochemical biosensor positioned to be exposed to at least a portion of said sample and adapted to generate a signal when exposed to acetone, said biosensor comprising;

a disposable physical support, adapted for insertion into and removal from said breath analysis apparatus by a user; and an enzyme able to selectively detect acetone in said sample, wherein said enzyme is supported by said disposable physical support; and a processor, coupled to said electrochemical biosensor, adapted to process an output from said electrochemical biosensor into a data signal.

* * * * *

UNITED STATES PATENT AND TRADEMARK OFFICE
CERTIFICATE OF CORRECTION

| | |
|---|---|
| PATENT NO. | : 7,364,551 B2 |
| APPLICATION NO. | : 10/492953 |
| DATED | : April 29, 2008 |
| INVENTOR(S) | : Jeffrey R. Allen et al. |

Page 1 of 1

It is certified that error appears in the above-identified patent and that said Letters Patent is hereby corrected as shown below:

Title page, item (73) should read as follows:
--Kemeta, LLC.--

Signed and Sealed this

Tenth Day of August, 2010

David J. Kappos
*Director of the United States Patent and Trademark Office*